(12) United States Patent
Scicinski et al.

(10) Patent No.: US 9,139,519 B2
(45) Date of Patent: Sep. 22, 2015

(54) ORGANONITRO THIOETHER COMPOUNDS AND MEDICAL USES THEREOF

(75) Inventors: Jan Scicinski, Saratoga, CA (US); Bryan T. Oronsky, Los Altos Hills, CA (US)

(73) Assignee: EPICENTRX, INC., Mountain View, CA (US)

( * ) Notice: Subject to any disclaimer, the term of this patent is extended or adjusted under 35 U.S.C. 154(b) by 0 days.

(21) Appl. No.: 14/349,004

(22) PCT Filed: May 18, 2012

(86) PCT No.: PCT/US2012/038592
§ 371 (c)(1),
(2), (4) Date: Aug. 11, 2014

(87) PCT Pub. No.: WO2013/052164
PCT Pub. Date: Apr. 11, 2013

(65) Prior Publication Data
US 2014/0349988 A1    Nov. 27, 2014

Related U.S. Application Data

(60) Provisional application No. 61/544,378, filed on Oct. 7, 2011.

(51) Int. Cl.
| | |
|---|---|
| A61K 31/397 | (2006.01) |
| C07D 205/04 | (2006.01) |
| A61K 31/19 | (2006.01) |
| A61K 31/198 | (2006.01) |
| A61K 31/215 | (2006.01) |
| A61K 31/337 | (2006.01) |
| A61K 45/06 | (2006.01) |
| A61N 5/10 | (2006.01) |

(52) U.S. Cl.
CPC .............. *C07D 205/04* (2013.01); *A61K 31/19* (2013.01); *A61K 31/198* (2013.01); *A61K 31/215* (2013.01); *A61K 31/337* (2013.01); *A61K 31/397* (2013.01); *A61K 45/06* (2013.01); *A61N 5/10* (2013.01)

(58) Field of Classification Search
None
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |
| 4,765,539 A | 8/1988 | Noakes et al. |
| 5,112,598 A | 5/1992 | Biesalski |
| 5,336,784 A | 8/1994 | Hiskey et al. |
| 5,521,203 A | 5/1996 | Adams et al. |
| 5,556,611 A | 9/1996 | Biesalski |
| 5,579,458 A | 11/1996 | Yokosuka et al. |
| 5,580,988 A | 12/1996 | Dave |
| 5,679,777 A | 10/1997 | Anderson et al. |
| 5,693,794 A | 12/1997 | Nielsen |
| 5,698,155 A | 12/1997 | Grosswald et al. |
| 5,950,619 A | 9/1999 | van der Linden et al. |
| 5,954,047 A | 9/1999 | Armer et al. |
| 5,970,974 A | 10/1999 | Van Der Linden et al. |
| 6,133,320 A | 10/2000 | Yallampalli et al. |
| 6,245,799 B1 | 6/2001 | Asselin et al. |
| 6,407,236 B1 | 6/2002 | Baraldi et al. |
| 7,163,958 B2 | 1/2007 | Earl et al. |
| 7,507,842 B2 | 3/2009 | Oehler et al. |
| 7,745,643 B2 | 6/2010 | Cannizzo et al. |
| 8,178,698 B2 | 5/2012 | Cannizzo et al. |
| 8,299,053 B2 | 10/2012 | Bednarski et al. |
| 8,664,247 B2 | 3/2014 | Scicinski et al. |
| 2002/0137770 A1 | 9/2002 | Nara et al. |
| 2004/0024057 A1 | 2/2004 | Earl et al. |
| 2004/0167212 A1 | 8/2004 | Bednarski et al. |
| 2006/0111272 A1 | 5/2006 | Roberts et al. |
| 2008/0255149 A1 | 10/2008 | Dobler et al. |
| 2008/0256149 A1 | 10/2008 | Bansal et al. |
| 2009/0093644 A1 | 4/2009 | Cannizzo et al. |
| 2009/0163466 A1 | 6/2009 | Bednarski et al. |

(Continued)

FOREIGN PATENT DOCUMENTS

| | | |
|---|---|---|
| DE | 10111049 A1 | 9/2002 |
| EP | 0412211 A1 | 2/1991 |

(Continued)

OTHER PUBLICATIONS

Akhavan, Jacqueline, "Explosives and Propellants," Kirk-Othmer Encyclopedia of Chemical Technology, Sep. 17, 2004, pp. 719-744.
Alderman, D., "A Review of Cellulose Ethers in Hydrophilic Matrices for Oral Controlled-Release Dosage Forms," *Int. J. Pharm. Tech. & Prod. Mfr.*, 1984, vol. 5, No. 3, pp. 1-9.
Ansari, Nabi G., et al., "Primary squamous cell carcinoma of the prostate: a rare clinicopathological entity. Report of 2 cases and review of literature," Urol. Int., 2001, pp. 216-219, vol. 66, No. 4 (abstract).

(Continued)

*Primary Examiner* — Michael Barker
(74) *Attorney, Agent, or Firm* — Goodwin Procter LLP

(57) ABSTRACT

The invention provides organonitro thioether compounds, compositions containing such compounds, isolated organonitro thioether compounds and methods for using such compounds and compositions to treat cancer in a patient. Exemplary organonitro thioether compounds described herein include 2-(3,3-dinitroazetidin-1-yl)-2-oxoethyl thioethers and variants thereof. Another aspect of the invention provides a pharmaceutical composition, comprising a pharmaceutically acceptable carrier and an organonitro thioether compound described herein, such as a compound of Formula I or II. Another aspect of the invention provides a method of treating cancer in a patient. The method comprises administering to a patient in need thereof a therapeutically effective amount of an organonitro thioether compound described herein, such as a compound of Formula I or II, to treat the cancer.

24 Claims, 1 Drawing Sheet

(56) References Cited

U.S. PATENT DOCUMENTS

| | | | |
|---|---|---|---|
| 2010/0247682 | A1 | 9/2010 | Gladwin et al. |
| 2011/0130572 | A1 | 6/2011 | Cannizzo et al. |
| 2011/0195947 | A1 | 8/2011 | Straessler et al. |
| 2012/0149678 | A1 | 6/2012 | Oronsky et al. |
| 2013/0053418 | A1 | 2/2013 | Scicinski et al. |

FOREIGN PATENT DOCUMENTS

| | | | |
|---|---|---|---|
| WO | WO-9532715 A1 | 12/1995 | |
| WO | WO-9636602 A1 | 11/1996 | |
| WO | WO-9816485 A1 | 4/1998 | |
| WO | WO-9916436 A1 | 4/1999 | |
| WO | WO-9959575 A1 | 11/1999 | |
| WO | WO-0006143 A1 | 2/2000 | |
| WO | WO-0177100 A2 | 10/2001 | |
| WO | WO-2004032864 A2 | 4/2004 | |
| WO | WO-2004098538 A2 | 11/2004 | |
| WO | WO-2004113281 A1 | 12/2004 | |
| WO | WO-2005046661 A2 | 5/2005 | |
| WO | WO-2007022121 A2 | 2/2007 | |
| WO | WO-2007022225 A2 | 2/2007 | |

OTHER PUBLICATIONS

Archibald et al., "Synthesis and X-ray Crystal Structure of 1,3,3-Trinitroazetidine," *J. Org. Chem.*, 1990, vol. 55, pp. 2920-2924.

Australian Examination Report No. 2 on patent application No. 2006279589, dated May 18, 2012.

Bamba et al., "Release Mechanisms in Gelforming Sustained Release Preparations," Int. J. Pharm., 1979, vol. 2, pp. 307-315.

Coburn et al., CAPLUS an 1998:567551, 27 pages.

Chawla et al., "Challenges in Polymorphism of Pharmaceuticals", CRIPS vol. 5, No. 1, Jan.-Mar. 2004, pp. 9-12.

Crowder et al., (1999) "Vibrational analysis of high-energy compounds: 1,3,3-trinitroazetidine and 1-acetyl-3, 3-dinitroazetidine," *Journal of Energetic Materials*, vol. 17(1), pp. 49-68.

Crowder et al., CAPLUS an 1999:171384.

Dave, P., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," *J. Org. Chem.*, 1996, vol. 61, pp. 5453-5455.

Dave, P.R. et al., "Convenient Acylative Dealkylation of Tertiary Amines," *Journal of Organic Chemistry*, 2000, vol. 65, pp. 1207-1209.

During et al., "Controlled Release of Dopamine from a Polymeric Brain Implant: In Vivo Characterization," *Annals of Neurology*, 1989, vol. 25, No. 4, pp. 351-356.

Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.

Feuer et al., "The Mannich reaction of certain dinitro alcohols with glycine and ethanolamine," *Journal of American Chemical Society*, 1954, vol. 76, pp. 5124-5126.

Garver et al., "Catalyzed Oxidative Nitration of Nitronate Salts," J. Org. Chem. 1985, vol. 50, No. 10, pp. 1699-1702.

Gladwin et al., "The Emerging Biology of the Nitrite Anion," in Nature Chemistry and Biology, 2005, vol. 1, pp. 308-314.

Goodson, J. Max, "Dental Applications," Chapter 6 of Medical Applications of Controlled Release, vol. II, pp. 115-138, CRC Press, Inc., Boca Raton, FL, copyright 1984.

Granelli, P. "SEL 1L and Sqaumous Cell Carcinoma of the Esophagus," *Clinical Cancer Research*, 2004, vol. 10, pp. 5857-5861.

Hiskey et al., "Preparation of 1-Substituted-3,3-Dinitroazetidines," *Journal of Energetic Materials* , 1999, vol. 17, pp. 233-254.

Hiskey et al., caplus an 1993:233785.

Hiskey et al., caplus an 1994:700750.

Hockel et al., "Tumor Hypoxia: Definitions and Current Clinical, Biologic, and Molecular Aspects,"*Journal of the National Cancer Institute*, 2001, vol. 93, No. 4, pp. 266-276.

Howard et al., "Intracerebral Drug Delivery in Rats with Lesion-Induced Memory Deficits," *J. Neursurg.*, 1989, vol. 71, pp. 105-112.

Huguenin et al., "Evaluation of the antitumoral potential of different nitric oxide-donating non-steroidal anti-inflamatory drugs (NO-NSAIDs) on human urological tumor cell lines", Cancer Letters 218 (2005), 163-170 (Abstract, pp. 165,169).

International Search Report and Written Opinion for PCT/US2011/064178 mailed Apr. 17, 2012 (8 pages).

International Search Report and Written Opinion for PCT/US2012/038592 mailed Aug. 10, 2012 (11 pages).

International Search Report for PCT/US2006/031917 mailed Jul. 20, 2007.

International Search Report for PCT/US2006/031722 mailed May 29, 2007.

International Search Report for PCT/US2011/021500 mailed May 3, 2011.

International Search Report and Written Opinion for PCT/US2012/058964, mailed Apr. 5, 2014, 14 pages.

International Search Report and Written Opinion for PCT/US2012/038592 mailed Aug. 10, 2012, 28 pages.

Jia, Q., et al., "NO donors with anticancer activity," Expert Opinion on Therapeutic Patents, vol. 12, No. 6 (2002), pp. 819-826, Great Britain.

Johnson, J. et al., "Relationships Between Drug Activity in NCI Preclinical in Vitro and in Vivo Models and Early Clinical Trials," *British Journal of Cancer*, 2001, pp. 1424-1431, vol. 84, No. 10.

Kashfi, Khosrow, et al., "Nitric Oxide-Donating Nonsteroidal Anti-Inflammatory Drugs Inhibit the Growth of Various Cultured Human Cancer Cells: Evidence of a Tissue Type-Independent Effect," *The Journal of Pharmacology and Experimental Therapeutics*, 2002, pp. 1273-1282, vol. 303, No. 3.

Katritzky et al., "Novel Syntheses of 1,3,3-Trinitroazetidine," J. Heterocyclic Chem., Mar.-Apr. 1994, vol. 31, pp. 271-275.

Konovalova, N.P., et al., "Nitric oxide donor increases the efficiency of cytostatic therapy and retards the development of drug resistance," *Nitric Oxide*, vol. 8, No. 1 (Feb. 2003), pp. 59-64.

Kornblum et al., "Oxidative Substitution of Nitroparaffin Salts," *J. Org. Chem.*, 1983, vol. 48, pp. 332-337.

Langer et al., "Chemical and Physical Structure of Polymers as Carriers for Controlled Release of Bioactive Agents: A Review," *JMS-Rev. Macromol. Chem. Phys.*, 1983, Ch. 23, pp. 61-126.

Langer, Robert S., et al., eds., "Medical Applications of Controlled Release," vol. 1, Classes of Systems, Ch. 2, pp. 42-67, CRC Press, Inc., Boca Raton, FL, copyright 1984.

Langer, Robert, "New Methods of Drug Delivery," Science, New Series, vol. 249, No. 4976, Sep. 28, 1990, pp. 1527-1533.

Levy, Robert J., "Inhibition of Calcification of Bioprosthetic Heart Valves by Local Controlled-Release Diphosphonate," Science, New Series, vol. 228, No. 4696, Apr. 12, 1985, pp. 190-192.

Ling, C., et al., "Phase I study of CM—Na combined with concurrent radiochemotherapy for advanced esophageal carcinoma (abstract)," Chinese Journal of Cancer, vol. 24, No. 5 (May 2005), (U.S. National Library of Medicine, Bethesda, MD, May 2005).

Lopez-Ferrer, Anna, et al., "Differences in the O-Glycosylation Patterns Between Lung Squamous Cell Carcinoma and Adenocarcinoma," Am. J. Clin. Pathol., 2002, pp. 749-755, vol. 118, American Society for Clinical Pathology.

Marchand et al., "A Novel Approach to the Synthesis of 1,3,3-Trinitroazetidine," J. Org Chem. 1995, vol. 60, No. 15, pp. 4943-4946.

Marchand, A. P. et al., "Additions of X-Y Across the C(3)-N σ-Bond in 1-Aza-3-ethylbicyclo[1.1.0]butane, Novel Routes to 3-Substituted Azetidines," *Journal of Organic Chemistry*, 1994, vol. 59, No. 18, pp. 5499-5501.

Maxwell, P.H., et al., "Hypoxia-inducible factor-1 modulates gene expression in solid tumors and influences both angiogenesis and tumor growth," Proc. Natl. Acad. Sci. USA, Jul. 1997, pp. 8104-8109, vol. 94, Medical Sciences.

McKenney, et al., "Synthesis and thermal properties of 1, 3-dinitro-3-(1', 3'-dinitroazetidein-3'-yl) azetidine (tndaz) and its admixtures with 1, 3, 3-trinitroazetidine (TNAZ)," Journal of Energetic Materials, 1998, vol. 16, pp. 199-235.

(56) References Cited

OTHER PUBLICATIONS

Mendenhall, William M., et al., "Radiation Therapy for Squamous Cell Carcinoma of the Tonsillar Region: A Preferred Alternative to Surgery?," Journal of Clinical Oncology, Jun. 2000, pp. 2219-2225, vol. 18, No. 11.

Morales-Suarez-Varela, Maria M., et al., "Impact of Nitrates in Drinking Water on Cancer Mortality in Valencia, Spain," European Journal of Epidemiology, 1995, pp. 15-21, vol. 11.

Muehlstaedt et al., CAPLUS, 1976:89768, 1 page.

Naimi, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., vol. 46, 2003, pp. 995-1004.

Nara, et al., CAPLUS an 2002:169585, 2002, 2 pages.

Newman et al., "Solid-state analysis of the active pharmaceutical ingredient in drug products", DDT vol. 8, No. 19, Oct. 2003, p. 898-905.

Nitrates and Nitrites Answers to Frequently Asked Questions, Ohio Bureau of Environmental Health, Health Assessment Section, Nov. 1, 2006, 2 pages.

Oxley J. et al., "Thermal Decomposition Pathways of 1,3,3-Trinitroazetidine (TNAZ), Related 3,3-Dinitroazetidium Salts, and $^{15}$N, $^{13}$C, and $^{2}$H Isotopomers," Journal of Physical Chemistry A, 1997, vol. 101, No. 24, pp. 4375-4383.

Padwa et al., "Diastereofacial selectivity in azomethine ylide cycloaddition reactions derived from chiral α-cyanoaminsilanes," Tetrahedron, 1985, vol. 41, No. 17, pp. 3529-3535.

Peiris, S. M. et al., "Structures of dinitroazetidine and three of its carbonyl derivatives," Journal of Chemical Crystallography, 2001, vol. 30, No. 10, pp. 647-653.

Prezioso, J.A., et al., "Genetic Toxicity Evaluation of 1, 3, 3-Trinitroazetidine, vol. IV: Summary Report on the Genotoxicity of TNAZ," AL/OE-TR-1994-0069 vol. IV of IV, Oct. 1994, 22 pages, Air Force Materiel Command, Wright-Patterson Air Force Base, Ohio.

Raleigh et al. "Pharmacokinetics of Isotretinoin (ISO) in Rats Following Oral Dosing or Aerosol Inhalation," British J. Cancer, 1999, vol. 80, Suppl. 2, 96, p. 269.

Remington, "The Science and Practice of Pharmacy," 19th Edition, 1995, vol. II, pp. 1495-1562, 1577-1614, and 1660-1692.

Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research, vol. 5, No. 4, pp. 739-745, Apr. 1999.

Sandler, G., "Clinical evaluation of propatylnitrate in angina pectoris," British Medical Journal, vol. 2, No. 5269 (Dec. 30, 1961), pp. 1741-1744.

Sauder, C. "A Preliminary Trial of the Programmable Implantable Medication System for Insulin Delivery," The New England Journal of Medicine, 1989, vol. 321, No. 9, pp. 574-579.

Sausville, Edward A., et al., "Contributions of Human Tumor Xenografts to Anticancer Drug Development," Cancer Research, 2006, pp. 3351-3354, vol. 66, No. 7.

Sefton, M., "Implantable Pumps," CRC Crit. Rev. Biomed. Eng., 1987, vol. 14, No. 3, pp. 201-237.

Shokeir, A., "Squamous Cell Carcinoma of the Bladder: pathology, diagnosis and treatment," BJU International, 2004, vol. 93, pp. 216-220.

Sikder et al., "1,3,3-Trinitroazetidine (TNAZ), a melt-cast explosive: synthesis, characterization and thermal behavior," Journal of Hazardous Materials, vol. 113, 2004, pp. 35-43.

Simpson, R.L., et al., "Characterization of TNAZ," UCRL-ID-119672, Dec. 14, 1994, Lawrence Livermore National Laboratory, 15 pages.

Smolen et al., "Controlled Drug Bioavailability," Drug Product Design and Performance, 1984, vol. 1, Ch. 7, pp. 203-237.

Stamler, J.S., et al., "Inhaled ethyl nitrite gas for persistent pulmonary hypertension in infants," The Lancet, Lancet Limited, vol. 360, No. 9350 (Dec. 21, 2002), p. 2077, Great Britain.

Straessler et al., "Development of a Safe and Efficient Two-Step Synthesis for Preparing 1-Bromoacetyl-3,3-dinitroazetidine, a Novel Clinical Anticancer Candidate," Organic Process Research & Development, 2012, vol. 16, pp. 512-517.

Strafford et al., "Bioreductive drugs into the next millennium," Anti-Cancer Drug Design, 1998, vol. 13, pp. 519-528.

Treat, Joseph, et al., "Liposome Encapsulated Doxorubicin Preliminary Results of Phase I and Phase II Trials," Liposomes in the Therapy of Infectious Diseases and Cancer, Proceedings of the Ciba-Geigy-Squibb-UCLA Colloquium at Lake Tahoe, CA, Feb. 16-20, 1988, pp. 353-365.

Verma et al., "Osmotically Controlled Oral Drug Delivery," Drug Dev. Ind. Pharm., 2000, vol. 26, No. 7, pp. 695-708.

Watt, Duncan S., et al., "Evaluation of 1,3,3-Trinitrozaetidine (TNAZ)—A High Performance Melt-Catable Explosive," Weapons Systems Division Aeronautical and Maritime Research Laboratory, Report No. DSTO-TR-1000, issue date Jul. 2000, 34 pages.

Watt, Duncan S., et al., "TNAZ Based Melt-Cast Explosives: Technology Review and AMRL Research Directions," Weapons Systems Division Aeronautical and Maritime Research Laboratory, Report DSTO-TR-0702, issue date Jul. 1998, 1-37 pages.

West, Anthony R., Solid State Chemistry and its Applications, 1988, pp. 358, and 365, Wiley, New York.

Wilson, et al., "Radiation-activated prodrugs as hypoxia-selective cytotoxins: model studies with nitroarylmethyl quaternary salts," Anti-Cancer Drug Design, 1998, vol. 13, pp. 663-685.

Written Opinion of the International Searching Authority for PCT/US2011/021500, mailed May 3, 2011.

Written Opinion of the International Searching Authority for PCT/US06/31722 mailed May 29, 2007.

Written Opinion of the International Searching Authority for PCT/US06/31917 mailed Jul. 20, 2007.

Yarmukhamedov et al., "One-step synthesis of substituted 3,5-dinitropiperidines and 1,5-dinitro-3,7-diazabicyclo(3.3.1)nonanes from 1,3-dinitropropanes," Russian Chemical Bulletin, International Edition, 2005, vol. 54, No. 2, pp. 414-420.

Yen, et al., "F-FDG Uptake in Squamous Cell Carcinoma of the Cervix Is Correlated with Glucose Transporter 1 Expression," The Journal of Nuclear Medicine, Jan. 2004, pp. 22-29, vol. 45, No. 1.

Zhang et al, caplus an 1998:460439.

ORGANONITRO THIOETHER COMPOUNDS AND MEDICAL USES THEREOF

CROSS REFERENCE TO RELATED APPLICATION

This application is a national stage entry of International Patent Application No. PCT/US2012/038592, filed May 18, 2012, which claims the benefit of and priority to U.S. Provisional Patent Application Ser. No. 61/544,378 filed Oct. 7, 2011, the contents of each of which are hereby incorporated by reference.

FIELD OF THE INVENTION

The invention provides organonitro thioether compounds, compositions containing such compounds, isolated compounds, and methods for using such compounds and compositions to treat cancer in a patient.

BACKGROUND

Cancer is a significant health problem despite the many advances made for detecting and treating this disease. Current strategies for managing cancer rely on early diagnosis and aggressive treatment. Treatment options often include surgery, radiotherapy, chemotherapy, hormone therapy, or a combination thereof. While such therapies provide a benefit to many patients, there is still a need for better therapeutic agents to treat various types of cancer.

Prostate cancer, breast cancer, and lung cancer are leading causes of cancer-related death. Prostate cancer is the most common form of cancer among males, with an estimated incidence of 30% in men over the age of 50. Moreover, clinical evidence indicates that human prostate cancer has the propensity to metastasize to bone, and the disease appears to progress inevitably from androgen dependent to androgen refractory status, leading to increased patient mortality. Breast cancer remains a leading cause of death in women. Its cumulative risk is relatively high; certain reports indicate that approximately one in eight women are expected to develop some type of breast cancer by age 85 in the United States. Likewise, lung cancer is a leading cause of cancer-related death, and non-small cell lung cancer (NSCLC) accounts for about 80% of these cases. Attempts to use serum protein markers for the early diagnosis of lung cancer have not yielded satisfactory results for routine screening, and newly developed early diagnostic methods using serum DNA as a diagnostic marker await further validation.

Accordingly, there is a need for new treatment regimes to treat these and other cancers. The present invention fulfills this need and provides other related advantages.

SUMMARY

The invention provides organonitro thioether compounds, compositions containing such compounds, isolated compounds, and methods for using such compounds and compositions to treat cancer in a patient. Various aspects and embodiments of the invention are described in further detail below.

Accordingly, one aspect of the invention provides a family of organonitro thioether compounds embraced by Formula I for use in the methods, compositions and kits described herein, wherein Formula I is represented by:

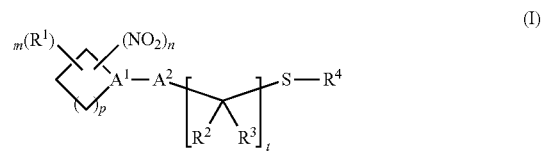

or a pharmaceutically acceptable salt or solvate thereof, wherein the variables are as defined in the detailed description. In certain embodiments, the compounds are provided in the form of an isolated compound of Formula I.

Another aspect of the invention provides a family of organonitro thioether compounds embraced by Formula II for use in the methods, compositions and kits described herein, wherein Formula II is represented by:

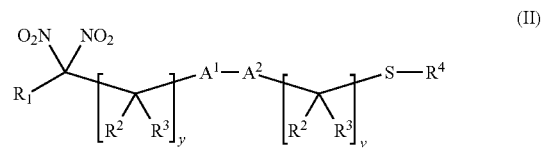

or a pharmaceutically acceptable salt or solvate thereof, wherein the variables are as defined in the detailed description. In certain embodiments, the compounds are provided in the form of an isolated compound of Formula II.

Another aspect of the invention provides a pharmaceutical composition, comprising a pharmaceutically acceptable carrier and an organonitro thioether compound described herein, such as a compound of Formula I or II.

Another aspect of the invention provides a method of treating cancer in a patient. The method comprises administering to a patient in need thereof a therapeutically effective amount of an organonitro thioether compound described herein, such as a compound of Formula I or II, to treat the cancer.

DETAILED DESCRIPTION OF THE INVENTION

Figure 1:
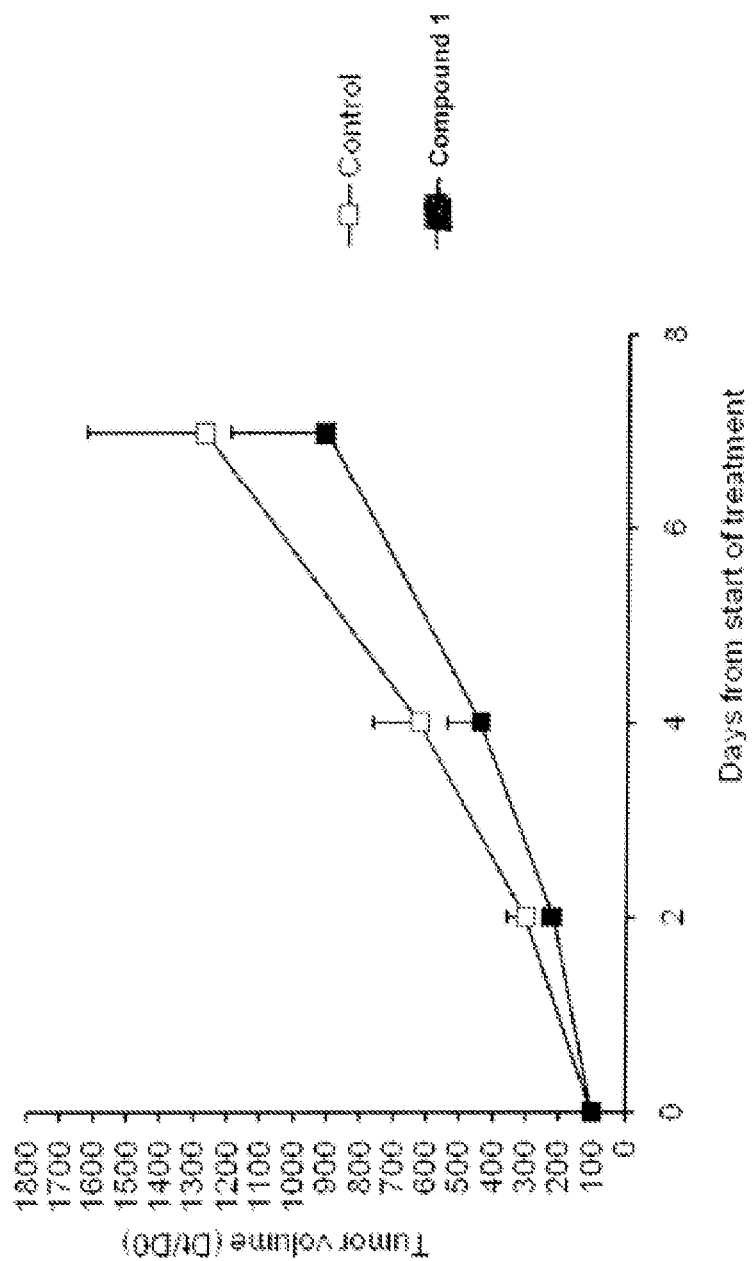
FIG. 1 is a graph showing SCCVII tumor volume in C3H mice that (a) received treatment with Compound 1 or (b) were not treated (i.e., control mice), as described in Example 6.

The invention provides organonitro thioether compounds, compositions containing such compounds, isolated compounds, and methods for using such compounds and compositions to treat cancer in a patient. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" as used herein refers to a saturated cyclic hydrocarbon, such as a cyclic hydrocarbon group of 3-10, or 3-6 carbon atoms, referred to herein as $C_3$-$C_{10}$cycloalkyl, and $C_3$-$C_6$cycloalkyl, respectively. Exemplary cycloalkyl groups include, but are not limited to, cyclopropyl, cyclobutyl, cyclopentyl, cyclohexyl, etc.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "aralkyl" refers to an alkyl group substituted with an aryl group.

The term "heteroaralkyl" refers to an alkyl group substituted with a heteroaryl group.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with halogen, alkyl, hydroxyl, or alkoxyl. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with halogen, alkyl, hydroxyl, or alkoxyl. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but are not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like.

The terms "amine" and "amino" are art-recognized and refer to both unsubstituted and substituted amines, e.g., a moiety represented by the general formula —$N(R^{50})(R^{51})$, wherein $R^{50}$ and $R^{51}$ each independently represent hydrogen, alkyl, cycloalkyl, heterocyclyl, alkenyl, aryl, aralkyl, or —$(CH_2)_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R_{61}$, where m and $R_{61}$ are described above.

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. It is understood that unless specified otherwise (e.g., using indicators of stereochemical configuration, such as wedge and/or dashed bonds), the chemical formulae encompass all geometric and stereoisomeric forms, including mixtures of geometric and/or stereoisomeric forms.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans. The term "non-anemic patient" refers to a patient that does not suffer from anemia.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "ABDNAZ" is art-recognized and refers to the following compound:

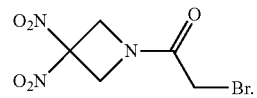

The abbreviation "TFA" is art-recognized and refers to trifluoroacetic acid.

As used herein, the term "isolated" refers to material that is removed from its original environment (e.g., the natural environment if it is naturally occurring).

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Organonitro Thioether Compounds for Use in the Methods, Compositions, and Kits Described Herein One aspect of the invention provides organonitro thioether compounds for use in the methods, compositions and kits described herein. In certain embodiments, the organonitro compound is a compound embraced by Formula I:

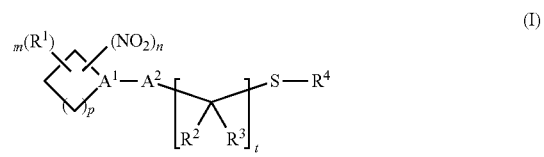

or a pharmaceutically acceptable salt or solvate thereof, wherein:

$A^1$ is N or $-C(R^5)-$;
$A^2$ is $-C(O)-$ or $-(C(R^6)_2)_xC(O)(C(R^6)_2)_x-$;
$R^1$ is $C_1$-$C_5$alkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is $-N(R^7)(R^8)$, $-N(R^7)C(O)-C_1$-$C_5$alkyl, $-N(R^7)C(O)-C_3$-$C_7$cycloalkyl, $-N(R^7)C(O)$-aryl, or $-N(R^7)C(O)-(C_1$-$C_5$alkylene)-$C(H)[N(R^7)(R^8)]-CO_2R^9$; and $X^2$ is $-CO_2R^{10}$ or $-C(O)N(R^7)-(C_1$-$C_5$alkylene)-$CO_2R^{10}$;

$R^5$ is hydrogen or $C_1$-$C_5$alkyl;

$R^6$ represents independently for each occurrence $C_1$-$C_6$alkyl, $C_1$-$C_5$haloalkyl, aryl, or aralkyl;

$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;

$R^9$ and $R^{10}$ each represent independently hydrogen, $C_1$-$C_5$alkyl, $C_3$-$C_7$cycloalkyl, aryl, or aralkyl;

n, p, and t are independently 1, 2, or 3; and m and x each represent independently for each occurrence 0, 1, 2, or 3.

In certain embodiments, $A^1$ is N. In certain embodiments, $A^2$ is —C(O)—.

In certain embodiments, $R^2$ and $R^3$ are hydrogen.

In certain embodiments, m is 0. In certain embodiments, n is 2. In certain other embodiments, n is 1. In certain embodiments, t is 1.

In certain embodiments, $R^4$ is —$CH_2C(H)(X^1)X^2$. In certain other embodiments, $R^4$ is

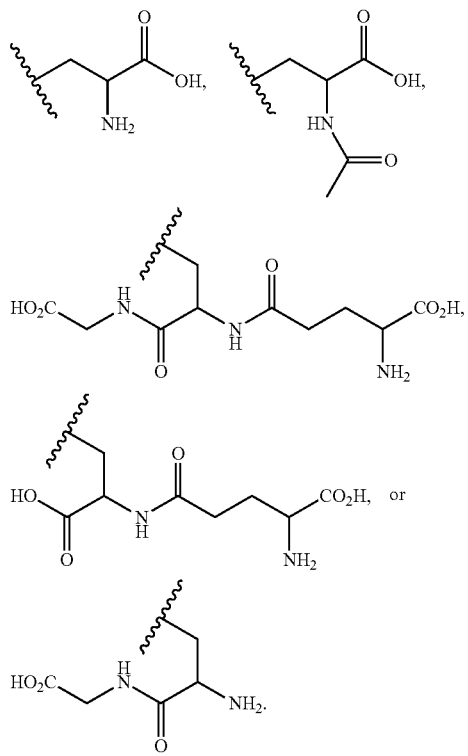

In certain other embodiments, $R^4$ is

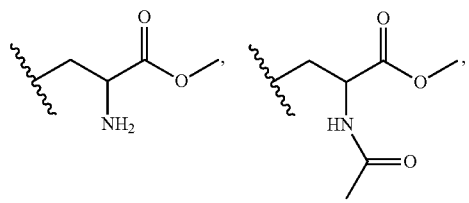

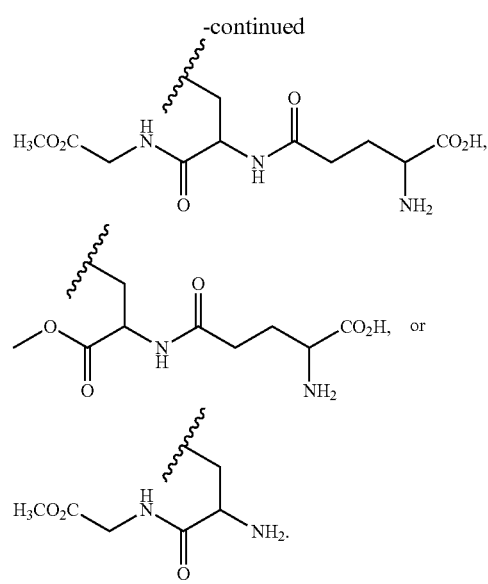

In certain embodiments, $X^1$ is —$N(R^7)(R^8)$, —$N(R^7)C(O)$—$C_1$-$C_5$alkyl, or —$N(R^7)C(O)$—$(C_1$-$C_5$alkylene)-C(H)[$N(R^7)(R^8)$]—$CO_2R^9$. In certain other embodiments, $X^1$ is —$NH_2$, —N(H)C(O)$CH_2$, or —N(H)C(O)$CH_2CH_2$C(H)($NH_2$)—$CO_2H$; and $X^2$ is —$CO_2H$, —$CO_2Me$, or —C(O)N(H)$CH_2CO_2H$. In certain other embodiments, $X^1$ is —$NH_2$ or —N(H)C(O)$CH_2CH_2$C(H)($NH_2$)—$CO_2H$; and $X^2$ is —$CO_2H$ or —C(O)N(H)$CH_2CO_2H$.

The description above describes multiple embodiments relating to compounds of Formula I. The patent application specifically contemplates all combinations of the embodiments. For example, the invention contemplates a compound of Formula I wherein $A^1$ is N, $A^2$ is —C(O)—, $R^2$ and $R^3$ are hydrogen, m is 0, n is 2, t is 1, and $R^4$ is —$CH_2C(H)(X^1)X^2$. Further, to illustrate, the invention contemplates a compound of Formula I wherein $A^1$ is N, $A^2$ is —C(O)—, $R^2$ and $R^3$ are hydrogen, m is 0, n is 1, t is 1, and $R^4$ is —$CH_2C(H)(X^1)X^2$.

In certain embodiments, the compound is a compound of Formula I-A:

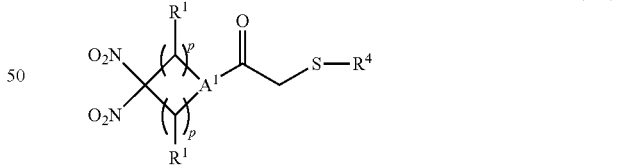

(I-A)

or a pharmaceutically acceptable salt or solvate thereof, wherein:

$A^1$ is N or C(H);

$R^1$ represents independently for each occurrence hydrogen or methyl;

$R^4$ is $C_1$-$C_5$alkyl substituted with one $X^1$ group and one $X^2$ group; wherein $X^1$ is —$NH_2$, —N(H)C(O)—$C_1$-$C_5$alkyl, or —N(H)C(O)—($C_1$-$C_5$alkylene)-C(H)($NH_2$)—$CO_2H$; and $X^2$ is —$CO_2H$, —$CO_2$—$C_1$-$C_5$alkyl, or —C(O)N(H)$CH_2CO_2H$; and p represents independently for each occurrence 1 or 2.

In certain embodiments, $R^4$ is —$CH_2C(H)(X^1)X^2$. In certain other embodiments, wherein $R^4$ is

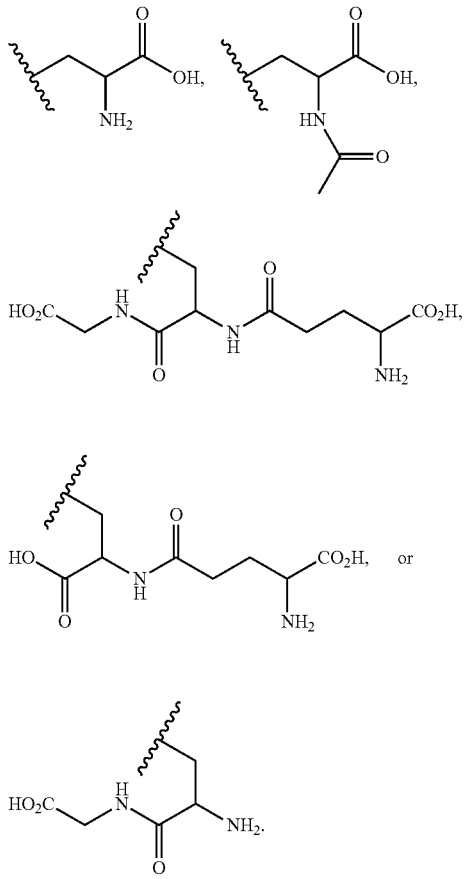

In certain embodiments, $X^1$ is —$NH_2$, —$N(H)C(O)CH_3$, or —$N(H)C(O)CH_2CH_2C(H)(NH_2)$—$CO_2H$; and $X^2$ is —$CO_2H$, —$CO_2Me$, or —$C(O)N(H)CH_2CO_2H$. In certain embodiments, $X^1$ is —$NH_2$ or —$N(H)C(O)CH_2CH_2C(H)(NH_2)$—$CO_2H$; and $X^2$ is —$CO_2H$ or —$C(O)N(H)CH_2CO_2H$.

In certain embodiments, the organonitro compound is represented by

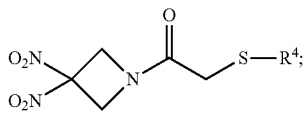

wherein $R^4$ is

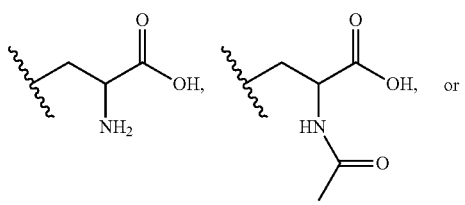

-continued

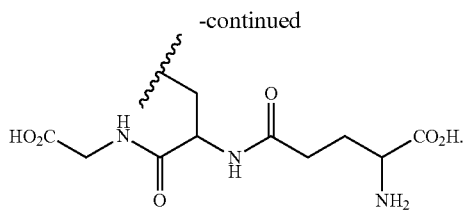

The description above describes multiple embodiments relating to compounds of Formula I-A. The patent application specifically contemplates all combinations of the embodiments. For example, the invention contemplates a compound of Formula I-A wherein $A^1$ is N, $R^1$ is hydrogen, $R^4$ is —$CH_2C(H)(X^1)X^2$, and p is 1.

In certain embodiments, the compound is a compound of Formula I-B:

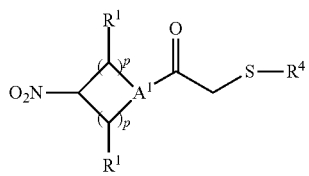

(I-B)

or a pharmaceutically acceptable salt or solvate thereof, wherein:

$A^1$ is N or C(H);

$R^1$ represents independently for each occurrence hydrogen or methyl;

$R^4$ is $C_1$-$C_5$alkyl substituted with one $X^1$ group and one $X^2$ group; wherein $X^1$ is —$NH_2$, —$N(H)C(O)$—$C_1$-$C_5$alkyl, or —$N(H)C(O)$—$(C_1$-$C_5$alkylene)-$C(H)(NH_2)$—$CO_2H$; and $X^2$ is —$CO_2H$, —$CO_2$—$C_1$-$C_5$alkyl, or —$C(O)N(H)$ $CH_2CO_2H$; and p represents independently for each occurrence 1 or 2.

In certain embodiments, $R^4$ is —$CH_2C(H)(X^1)X^2$. In certain other embodiments, wherein $R^4$ is

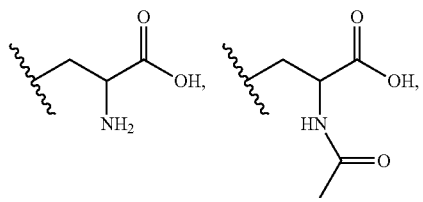

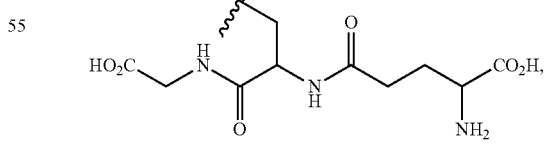

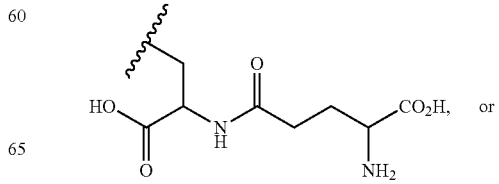

-continued

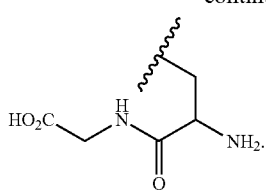

The description above describes multiple embodiments relating to compounds of Formula I-B. The patent application specifically contemplates all combinations of the embodiments. For example, the invention contemplates a compound of Formula I-B wherein $A^1$ is N, $R^1$ is hydrogen, $R^4$ is —$CH_2C(H)(X^1)X^2$, and p is 1.

In certain embodiments, the compound is one of the following:

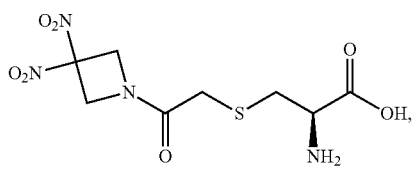

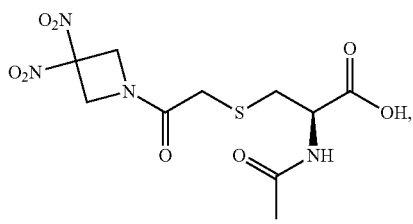

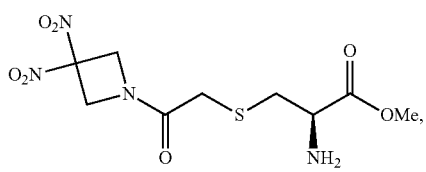

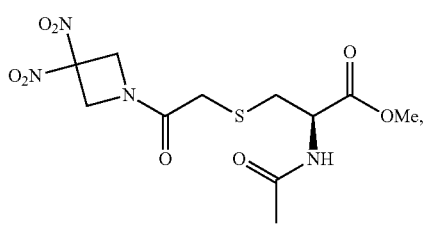

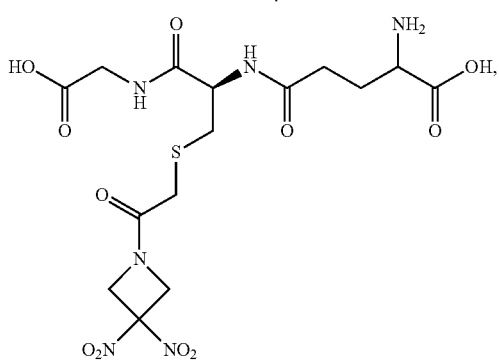

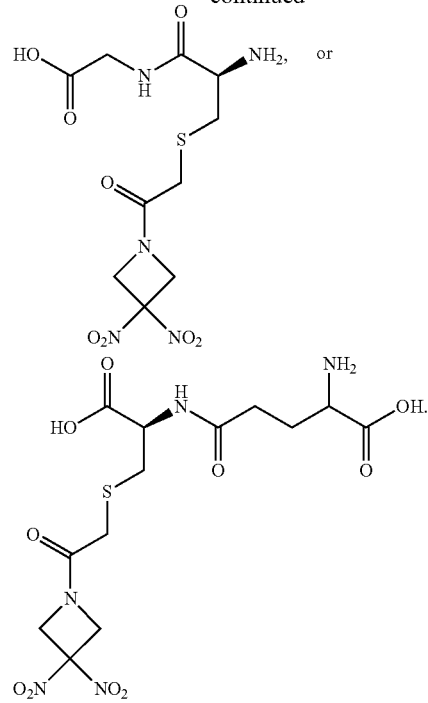

In certain embodiments, the compound is one of the foregoing or a pharmaceutically acceptable salt thereof.

In certain other embodiments, the organonitro compound is a compound embraced by Formula II:

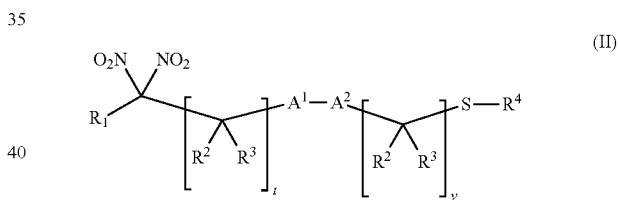

(II)

or a pharmaceutically acceptable salt or solvate thereof: wherein:

$A^1$ is —N($R^5$)— or —C($R^2$)($R^3$)—;

$A^2$ is —C(O)— or —(C($R^6$)$_2$)$_x$ C(O)(C($R^6$)$_2$)$_x$—;

$R^1$ is $C_1$-$C_5$alkyl or $C_3$-$C_7$cycloalkyl;

$R^2$ and $R^3$ each represent independently for each occurrence hydrogen or $C_1$-$C_5$alkyl; or $R^2$ and $R^3$ are taken together with the carbon atom to which they are attached to form a carbocyclic ring;

$R^4$ is $C_1$-$C_5$alkyl substituted with one $X^1$ group and one $X^2$ group; wherein $X^1$ is —N($R^7$)($R^8$), —N($R^7$)C(O)—$C_1$-$C_5$alkyl, —N($R^7$)C(O)—$C_3$-$C_7$cycloalkyl, —N($R^7$)C(O)-aryl, —N($R^7$)C(O)-aralkyl, or —N($R^7$)C(O)—($C_1$-$C_5$alkylene)-C(H)[N($R^7$)($R^8$)]—$CO_2R^9$; and $X^2$ is —$CO_2R^{10}$ or —C(O)N($R^7$)—($C_1$-$C_5$alkylene)-$CO_2R^{10}$;

$R^5$ is hydrogen or $C_1$-$C_5$alkyl;

$R^6$ represents independently for each occurrence $C_1$-$C_5$alkyl, $C_1$-$C_5$haloalkyl, aryl, or aralkyl;

$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;

$R^9$ and $R^{10}$ each represent independently hydrogen, $C_1$-$C_5$alkyl, $C_3$-$C_7$cycloalkyl, aryl, or aralkyl;

t and v are independently 1, 2, or 3; and x represents independently for each occurrence 0, 1, 2, or 3.

In certain embodiments, $A^1$ is N. In certain embodiments, $A^2$ is —C(O)—.

In certain embodiments, $R^2$ and $R^3$ are hydrogen.

In certain embodiments, m is 0. In certain embodiments, n is 2. In certain other embodiments, n is 1. In certain embodiments, wherein t is 1. In certain embodiments, wherein v is 1.

In certain embodiments, $R^4$ is —CH$_2$C(H)(X$^1$)X$^2$. In certain other embodiments, $R^4$ is

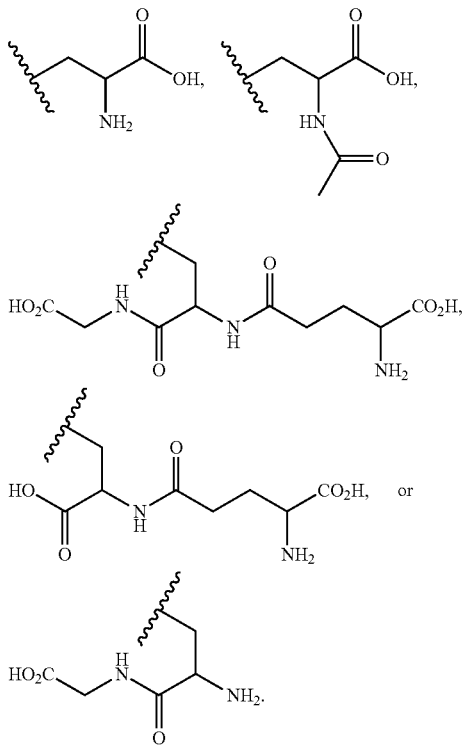

In certain other embodiments, $R^4$ is

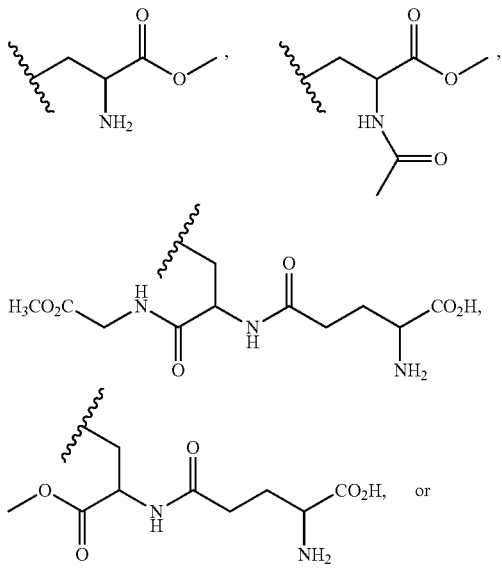

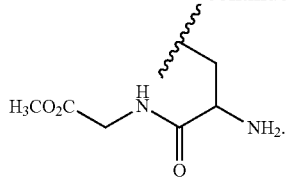

In certain embodiments, $X^1$ is —N(R$^7$)(R$^8$), —N(R$^7$)C(O)—C$_1$-C$_5$alkyl, or —N(R$^7$)C(O)—(C$_1$-C$_5$alkylene)-C(H)[N(R$^7$)(R$^8$)]—CO$_2$R$^9$. In certain other embodiments, $X^1$ is —NH$_2$, —N(H)C(O)CH$_2$, or —N(H)C(O)CH$_2$CH$_2$C(H)(NH$_2$)—CO$_2$H; and $X^2$ is —CO$_2$H, —CO$_2$Me, or —C(O)N(H)CH$_2$CO$_2$H. In certain other embodiments, $X^1$ is —NH$_2$ or —N(H)C(O)CH$_2$CH$_2$C(H)(NH$_2$)—CO$_2$H; and $X^2$ is —CO$_2$H or —C(O)N(H)CH$_2$CO$_2$H.

The description above describes multiple embodiments relating to compounds of Formula II. The patent application specifically contemplates all combinations of the embodiments. For example, the invention contemplates a compound of Formula II wherein $A^1$ is N, $A^2$ is —C(O)—, $R^2$ and $R^3$ are hydrogen, t is 1, v is 1, and $R^4$ is —CH$_2$C(H)(X$^1$)X$^2$.

In certain embodiments, the invention provides compounds of Formula I in isolated form. In another embodiment, the isolated compound of Formula I is substantially pure (that is having a purity of at least about 70%, 80%, 90%, 95%, or 99% by weight).

In certain embodiments, the invention provides compounds of Formula I-A in isolated form. In another embodiment, the isolated compound of Formula I-A is substantially pure (that is having a purity of at least about 70%, 80%, 90%, 95%, or 99% by weight). For example, in certain embodiments, the isolated compound may be one of the following isolated compounds:

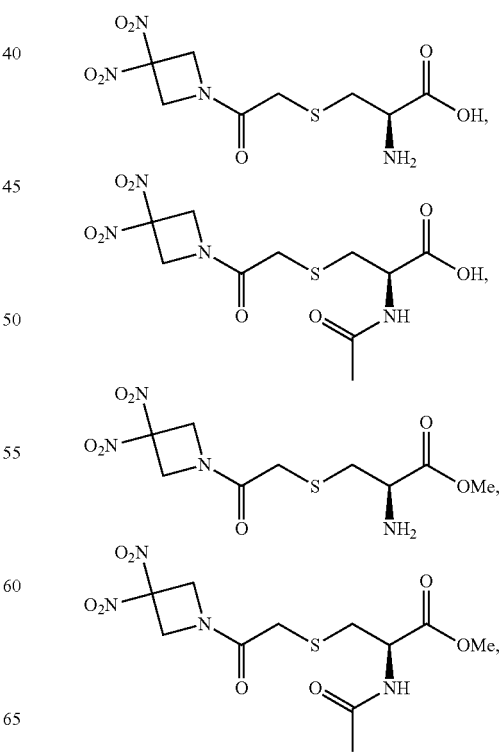

15
-continued

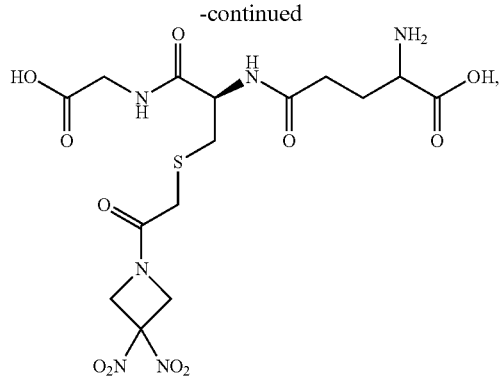

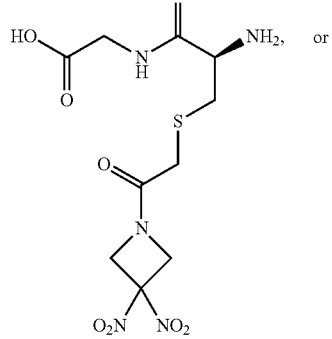

16
-continued

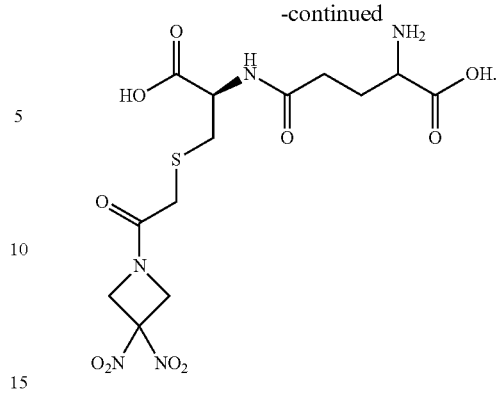

In certain embodiments, the isolated compound is one of the foregoing or a pharmaceutically acceptable salt thereof.

In certain other embodiments, the invention provides compounds of Formula II in isolated form. In another embodiment, the isolated compound of Formula I is substantially pure (that is having a purity of at least about 70%, 80%, 90%, 95%, or 99% by weight).

In certain other embodiments, the compound is one of the compounds listed in Tables 1, 2, or 3 below or a pharmaceutically acceptable salt or solvate thereof.

TABLE 1

| Compound No. | X | Y |
|---|---|---|
| I-1 | ⸺S-CH2-CH(NH2)-COOH | ⸺N(azetidine-3,3-(NO2)2) |
| I-2 | ⸺S-CH2-CH(NH2)-COOH | ⸺N(azetidine-3-NO2) |
| I-3 | ⸺S-CH2-CH(NH2)-COOH | ⸺N(2-methyl-3,3-dinitroazetidine) |
| I-4 | ⸺S-CH2-CH(NH2)-COOH | ⸺(3-nitrocyclobutyl) |
| I-5 | ⸺S-CH2-CH(NH2)-COOH | ⸺(3,3-dinitrocyclobutyl) |

TABLE 1-continued
$$\underset{X}{\diagdown}\overset{O}{\underset{}{\parallel}}\diagup Y$$
| Compound No. | X | Y |
|---|---|---|
| I-6 | 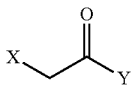 | 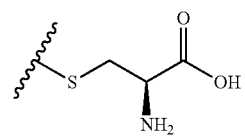 [SMILES: *SC[C@H](N)C(=O)O] |
| I-7 | 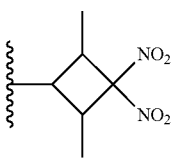 [SMILES: *C1C(C)C([N+](=O)[O-])([N+](=O)[O-])C1C] | 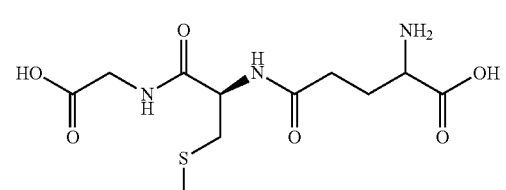 |
| I-8 | 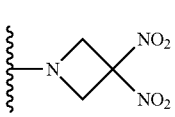 | 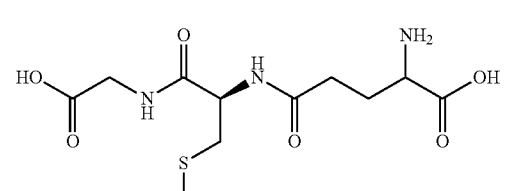 |
| I-9 | 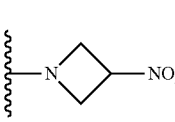 | 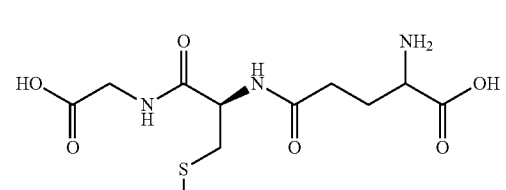 |
| I-10 | 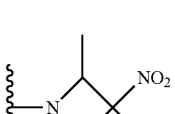 | 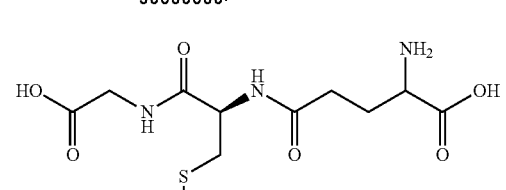 |
| I-11 | 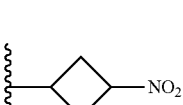 | 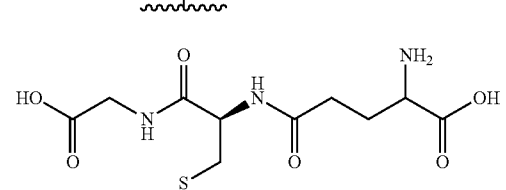 |
| I-12 |  | 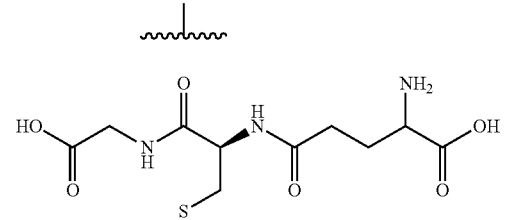 |

TABLE 1-continued

| Compound No. | X | Y |
|---|---|---|
| I-13 | S-Cys(Ac) | azetidine-3,3-dinitro (N-linked) |
| I-14 | S-Cys(Ac) | 2-methyl-azetidine-3,3-dinitro (N-linked) |
| I-15 | S-Cys(Ac) | 3,3-dinitrocyclobutyl |
| I-16 | Cys-Gly (S-linked) | azetidine-3,3-dinitro (N-linked) |
| I-17 | Cys-Gly (S-linked) | 2-methyl-azetidine-3,3-dinitro (N-linked) |
| I-18 | Cys-Gly (S-linked) | 3,3-dinitrocyclobutyl |
| I-19 | γ-Glu-Cys (S-linked) | azetidine-3,3-dinitro (N-linked) |

TABLE 1-continued

| Compound No. | X | Y |
|---|---|---|
| I-20 | cysteine-γ-glutamyl (glutathione-like fragment via S) | 3,3-dinitrocyclobutyl |
| I-21 | S-linked L-cysteine methyl ester | 3,3-dinitroazetidin-1-yl |
| I-22 | S-linked L-cysteine methyl ester | 3,3-dinitrocyclobutyl |
| I-23 | S-linked N-acetyl-L-cysteine methyl ester | 3,3-dinitroazetidin-1-yl |
| I-24 | S-linked N-acetyl-L-cysteine methyl ester | 3,3-dinitrocyclobutyl |
| I-25 | S-linked N-cyclopentyl-L-cysteine | 3,3-dinitroazetidin-1-yl |
| I-26 | S-linked N-cyclopropyl-L-cysteine | 3,3-dinitroazetidin-1-yl |

TABLE 1-continued
| Compound No. | X | Y |
|---|---|---|
| I-27 | 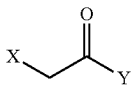 | 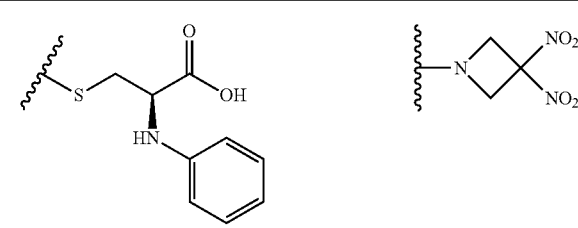 |
| I-28 | 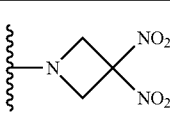 | 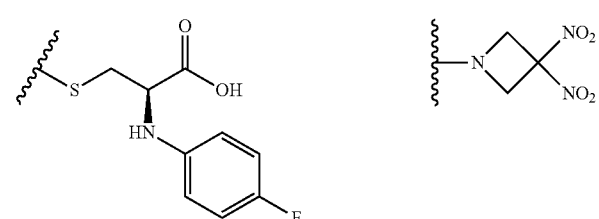 |
| I-29 | 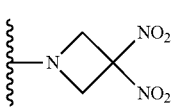 | 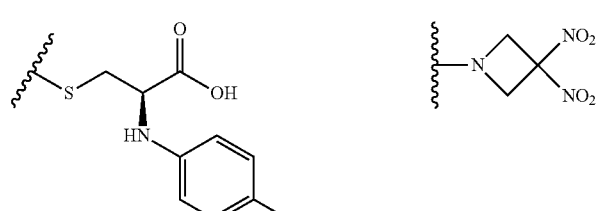 |
| I-30 | 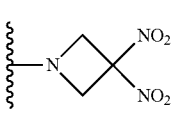 | 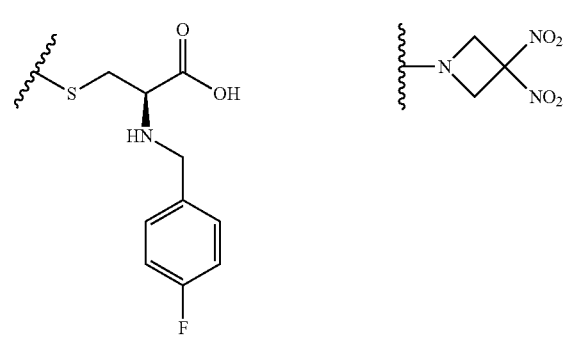 |
| I-31 | 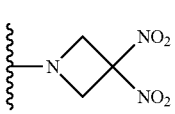 | 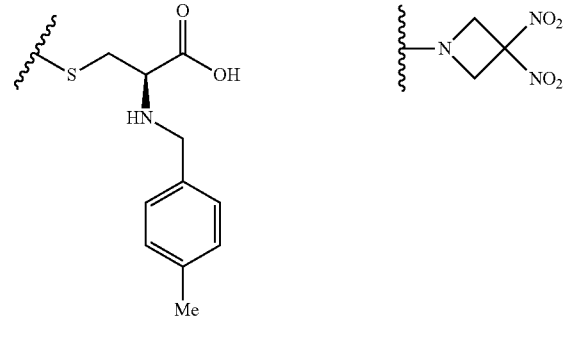 |

TABLE 1-continued

| Compound No. | X | Y |
|---|---|---|
| I-32 | N-acetylcysteine linked via S | 3,3-dinitroazetidin-1-yl |
| I-33 | Glutathione linked via cysteine S | 3,3-dinitroazetidin-1-yl |
| I-34 | Cysteine linked via S | 3,3-dinitroazetidin-1-yl |
| I-35 | Cys-Gly dipeptide linked via cysteine S | 3,3-dinitroazetidin-1-yl |
| I-36 | γ-Glu-Cys dipeptide linked via cysteine S | 3,3-dinitroazetidin-1-yl |
| I-37 | Cysteine methyl ester linked via S | 3,3-dinitroazetidin-1-yl |
| I-38 | N-acetylcysteine methyl ester linked via S | 3,3-dinitroazetidin-1-yl |

TABLE 1-continued
| Compound No. | X | Y |
|---|---|---|
| I-39 | 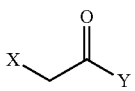 | 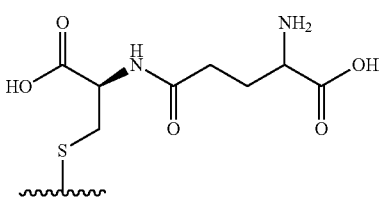 [SMILES: *SC[C@H](NC(=O)CCC(N)C(=O)O)C(=O)O] |
| I-40 | 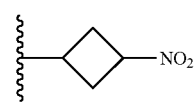 | 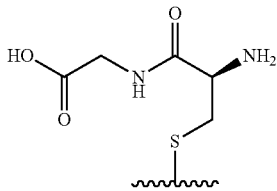 [SMILES: *SC[C@H](N)C(=O)NCC(=O)O] |
| I-41 | 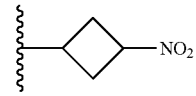 | 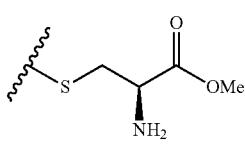 |
| I-42 | 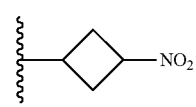 [SMILES: *C1CC([N+](=O)[O-])C1] | 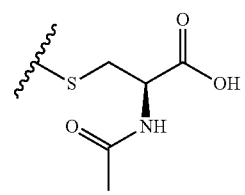 [SMILES: *SC[C@H](NC(C)=O)C(=O)O] |
| I-43 | 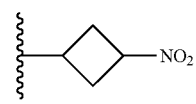 | 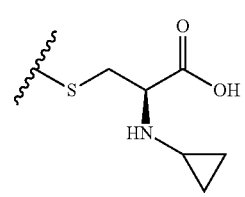 [SMILES: *SC[C@H](NC1CC1)C(=O)O] |
| I-44 | 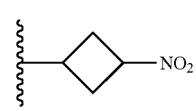 [SMILES: *C1CC([N+](=O)[O-])C1] | 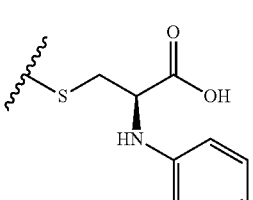 |
| I-45 | 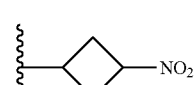 | 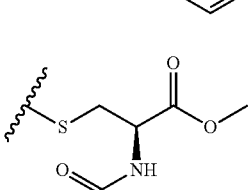 |

TABLE 2

| Compound No. | X | A | Y |
|---|---|---|---|
| II-1 | L-cysteine (S-linked) | —CH₂C(O)— | N-linked 3,3-dinitroazetidine |
| II-2 | L-cysteine (S-linked) | —CH₂C(O)— | 3,3-dinitrocyclobutyl |
| | glutathione (S-linked tripeptide: Glu-Cys-Gly) | | |
| II-3 | glutathione (S-linked tripeptide: Glu-Cys-Gly) | —CH₂C(O)— | N-linked 3,3-dinitroazetidine |
| II-4 | glutathione (S-linked tripeptide: Glu-Cys-Gly) | —CH₂C(O)— | 3,3-dinitrocyclobutyl |
| II-5 | L-cysteine (S-linked) | —C(O)CH₂CH₂— | N-linked 3,3-dinitroazetidine |
| II-6 | L-cysteine (S-linked) | —C(O)CH₂CH₂— | 3,3-dinitrocyclobutyl |
| II-7 | glutathione (S-linked tripeptide: Glu-Cys-Gly) | —C(O)CH₂CH₂— | N-linked 3,3-dinitroazetidine |

TABLE 2-continued
| Compound No. | X | A | Y |
|---|---|---|---|
| II-8 | 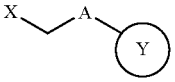 | —C(O)CH₂CH₂— | 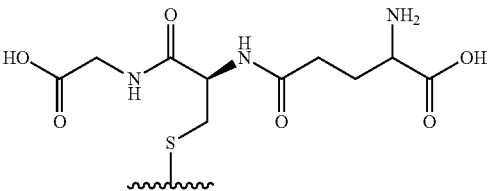 [SMILES: *SC[C@H](NC(=O)CCC(N)C(=O)O)C(=O)NCC(=O)O] |
| II-9 | 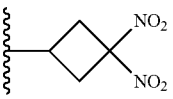 | —CH₂— | 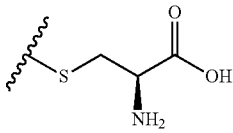 |
| II-10 |  | —CH₂— | 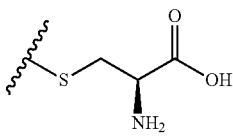 |
| II-11 | 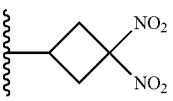 | —CH₂— | 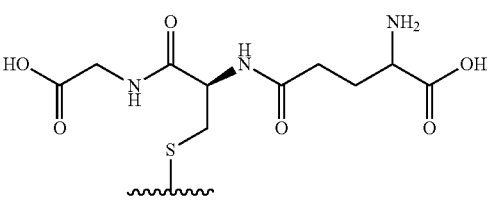 [SMILES: *SC[C@H](NC(=O)CCC(N)C(=O)O)C(=O)NCC(=O)O] |
| II-12 |  | —CH₂— | 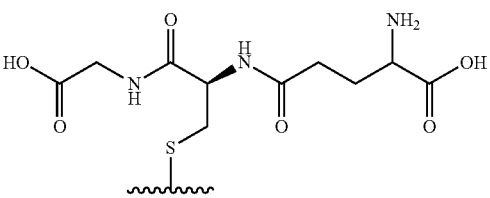 [SMILES: *SC[C@H](NC(=O)CCC(N)C(=O)O)C(=O)NCC(=O)O] |
| II-13 |  | —CH₂C(O)— | 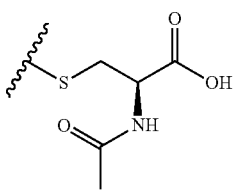 [SMILES: *SC[C@H](NC(C)=O)C(=O)O] |
| II-14 |  | —CH₂C(O)— | 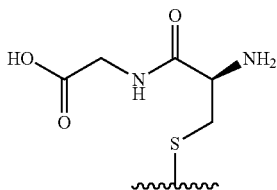 [SMILES: *SC[C@H](N)C(=O)NCC(=O)O] |
| II-15 | 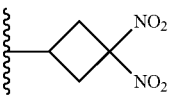 | —CH₂C(O)— | 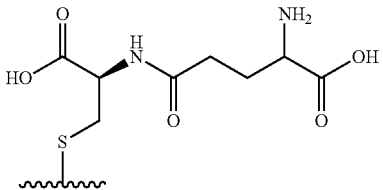 [SMILES: *SC[C@H](NC(=O)CCC(N)C(=O)O)C(=O)O] |

TABLE 2-continued

| Compound No. | X | A | Y |
|---|---|---|---|
| II-16 | *S-Cys(Ac)-OH* | —C(O)CH₂CH₂— | *N-azetidine-3,3-diNO₂* |
| II-17 | *Gly-Cys-S* | —C(O)CH₂CH₂— | *cyclobutane-3,3-diNO₂* |
| II-18 | *γ-Glu-Cys-S* | —C(O)CH₂CH₂— | *cyclobutane-3,3-diNO₂* |
| II-19 | *S-Cys(Ac)-OH* | —CH₂— | *N-azetidine-3,3-diNO₂* |
| II-20 | *Gly-Cys-S* | —CH₂— | *cyclobutane-3,3-diNO₂* |
| II-21 | *γ-Glu-Cys-S* | —CH₂— | *N-azetidine-3,3-diNO₂* |
| II-22 | *S-Cys(N-cyclopropyl)-OH* | —CH₂C(O)— | *N-azetidine-3,3-diNO₂* |

TABLE 2-continued
| Compound No. | X | A | Y |
|---|---|---|---|
| II-23 | 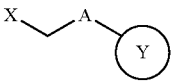 | —C(O)CH₂CH₂— | 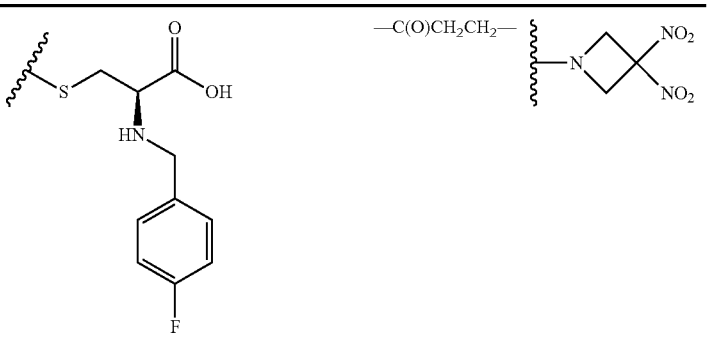 |
| II-24 | 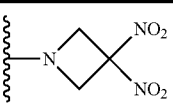 | —CH₂— | 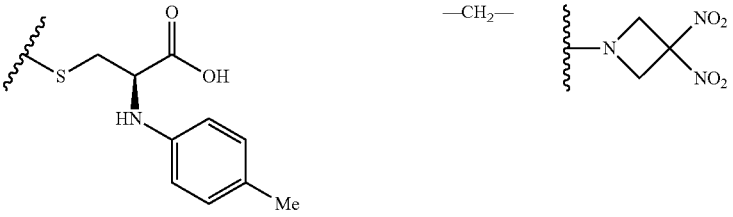 |
| II-25 | 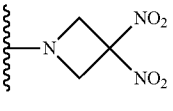 [SMILES: *N1CC([N+](=O)[O-])([N+](=O)[O-])C1] | —CH₂C(O)— |  |
| II-26 | 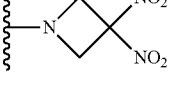 | —C(O)CH₂CH₂— | 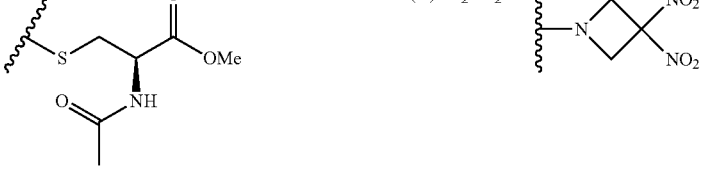 |
| II-27 | 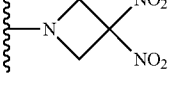 | —CH₂— |  |
| II-28 | 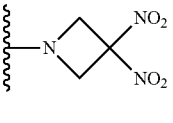 [SMILES: *N1CC([N+](=O)[O-])([N+](=O)[O-])C1] | —CH₂C(O)— |  |
| II-29 | 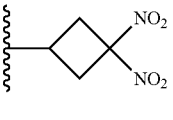 | —CH₂C(O)— |  |

TABLE 2-continued

| Compound No. | X | A | Y |
|---|---|---|---|
| II-30 | S-CH2-CH(NH2)-COOH (cysteine via S) | —CH2C(O)— | cyclobutane-3,3-dinitro |
| II-31 | glutathione (via S of Cys) | —CH2C(O)— | azetidine-N-, 3,3-dinitro |
| II-32 | glutathione (via S of Cys) | —CH2C(O)— | cyclobutane-3,3-dinitro |
| II-33 | N-acetyl cysteine (via S) | —C(O)CH2CH2— | azetidine-N-, 3,3-dinitro |
| II-34 | Gly-Cys (via S of Cys) | —CH2— | azetidine-N-, 3,3-dinitro |
| II-35 | γ-Glu-Cys (via S of Cys) | —CH2C(O)— | azetidine-N-, 3,3-dinitro |

TABLE 3
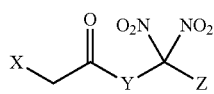
| Compound No. | X | Y | Z |
|---|---|---|---|
| III-1 | cysteine (S-linked) | —N(H)CH₂— | methyl |
| III-2 | glutathione (S-linked) | —N(H)CH₂— | methyl |
| III-3 | glutathione (S-linked) | —N(H)CH₂— | ethyl |
| III-4 | cysteine (S-linked) | —N(H)CH₂— | n-pentyl |
| III-5 | cysteine (S-linked) | —N(H)CH₂— | hydrogen |
| III-6 | glutathione (S-linked) | —N(H)CH₂CH₂— | methyl |
| III-7 | N-acetyl cysteine methyl ester (S-linked) | —N(H)(CH₂)₄— | methyl |
| III-8 | cysteine (S-linked) | —N(CH₃)CH₂— | methyl |

TABLE 3-continued

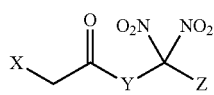

| Compound No. | X | Y | Z |
|---|---|---|---|
| III-9 | [L-cysteine with γ-glutamyl amide, HOOC-CH(NH)-CH2-S~ connected to Glu-OH/NH2] | —N(CH3)(CH2)3— | methyl |
| III-10 | [glycyl-cysteine: HOOC-CH2-NH-C(O)-CH(NH2)-CH2-S~] | —N(H)C(CH3)(H)— | methyl |
| III-11 | [~S-CH2-CH(NH2)-C(O)OMe] | —N(H)C(CH3)(H)CH2— | methyl |
| III-12 | [~S-CH2-CH(NHAc)-C(O)OMe] | —CH2— | methyl |
| III-13 | [~S-CH2-CH(NH-cyclopentyl)-C(O)OH] | —(CH2)2— | methyl |
| III-14 | [~S-CH2-CH(NH-cyclopropyl)-C(O)OH] | —CH2— | ethyl |
| III-15 | [~S-CH2-CH(NH-phenyl)-C(O)OH] | —(CH2)4— | isopropyl |

TABLE 3-continued structure: X-C(=O)-Y-C(NO₂)(NO₂)-Z

| Compound No. | X | Y | Z |
|---|---|---|---|
| III-16 | L-cysteine S-linked, N-(4-fluorophenyl) | —(CH₂)₂— | n-pentyl |
| III-17 | L-cysteine S-linked, N-(4-methylphenyl) | —CH₂— | hydrogen |
| III-18 | L-cysteine S-linked, N-(4-fluorobenzyl) | —CH₂CH₂C(CH₃)₂— | methyl |
| III-19 | L-cysteine S-linked (free NH₂) | —CH₂C(CH₃)₂CH₂— | methyl |
| III-20 | L-cysteine S-linked, N-cyclopropyl | —N(H)CH₂— | methyl |
| III-21 | L-cysteine S-linked, N-(4-methylphenyl) | —N(H)CH₂— | ethyl |

TABLE 3-continued

| Compound No. | X | Y | Z |
|---|---|---|---|
| III-22 | *HOOC-CH2-NH-C(=O)-CH(NH2)-CH2-S~* (glycyl-cysteinyl) | —N(CH3)CH2— | methyl |
| III-23 | *~S-CH2-CH(NHAc)-COOH* (N-acetyl-L-cysteinyl) | —(CH2)2— | methyl |
| III-24 | *HOOC-CH(NH-)-CH2-S~* linked to glutamyl (γ-Glu-Cys) | —N(H)CH2— | methyl |
| III-25 | *HOOC-CH2-NH-C(=O)-CH(NH2)-CH2-S~* | —N(H)CH2— | ethyl |
| III-26 | *~S-CH2-CH(NHAc)-COOH* | —N(CH3)CH2— | methyl |
| III-27 | *~S-CH2-CH(NH-cyclopentyl)-COOH* | —(CH2)2— | methyl |
| III-28 | *~S-CH2-CH(NH-(4-fluorophenyl))-COOH* | —N(H)CH2— | methyl |

TABLE 3-continued
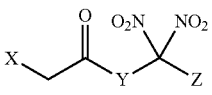
| Compound No. | X | Y | Z |
|---|---|---|---|
| III-29 | 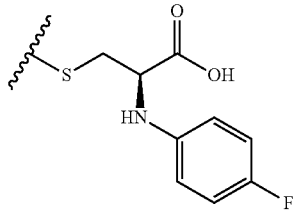 [SMILES: *SC[C@H](Nc1ccc(F)cc1)C(=O)O] | —N(CH₃)CH₂— | methyl |
| III-30 | 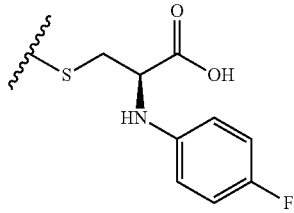 [SMILES: *SC[C@H](Nc1ccc(F)cc1)C(=O)O] | —N(H)CH₂— | methyl |
| III-31 | 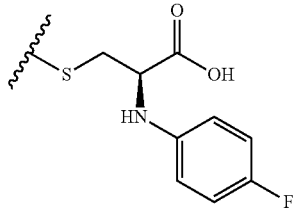 [SMILES: *SC[C@H](Nc1ccc(F)cc1)C(=O)O] | —N(CH₃)CH₂— | methyl |
| III-32 | 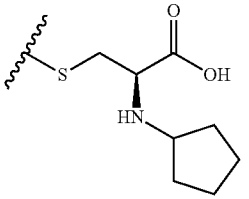 [SMILES: *SC[C@H](NC1CCCC1)C(=O)O] | —N(H)CH₂— | methyl |
| III-33 | 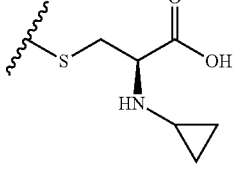 | —N(CH₃)CH₂— | methyl |
| III-34 | 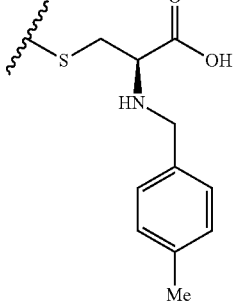 | —N(H)CH₂— | methyl |

TABLE 3-continued
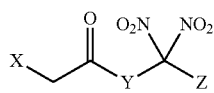
| Compound No. | X | Y | Z |
|---|---|---|---|
| III-35 | S-cysteine-NH-(4-methylphenyl) | —N(CH₃)CH₂— | methyl |
| III-36 | S-cysteine-NH-CH₂-(4-methylphenyl) | —(CH₂)₂— | methyl |
| III-37 | S-cysteine-NH-(4-methylphenyl) | —N(H)CH₂— | n-pentyl |
| III-38 | S-cysteine-NH-cyclopropyl | —N(CH₃)CH₂— | methyl |
| III-39 | S-cysteine-NH-CH₂-(4-fluorophenyl) | —N(H)CH₂CH₂— | ethyl |
| III-40 | S-cysteine-NH₂ | —N(H)CH₂— | methyl |

TABLE 3-continued

[Structure: X-C(=O)-C(Y)(O2N)(NO2)-Z]

| Compound No. | X | Y | Z |
|---|---|---|---|
| III-41 | [Structure: HO-CH2-C(=O)-NH-CH(CH2-S-~)-C(=O)-NH-CH(C(=O)OH)-CH2-CH2-C(=O)-NH2] (with NH2 label) | —N(H)CH2— | methyl |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme 1 depicts a general method for preparing cyclic geminal di-nitro compounds. In the first step, chloro epoxide A1 is reacted with t-butylamine to provide hydroxy heterocyclic compound B1. Mesylation of the hydroxyl group of heterocyclic compound B1 with methylsulfonyl chloride gives mesylate C1, which upon reacting with $NaNO_2$ generates cyclic mono-nitro compound D1. Further nitration of compound D1 can be carried out using $NaNO_2$ in the presence of $Na_2S_2O_8$ and $K_3Fe(CN)_6$ to provide geminal di-nitro heterocyclic compound E1. A three-step procedure provides final compound G1, which involves reaction of compound E1 with boron trifluoride etherate, acylation with acetyl bromide F, and thiolation to provide compound G1. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein.

This synthetic procedure illustrated in Scheme 1 and described above is contemplated to be applicable to preparing compounds having various substituents at the $R_1$, $R_2$, $R_3$ and $R_4$ positions. If a particular epoxide compound embraced by A1 should contain a functional group sensitive to one or more of the synthetic transformations in Scheme 1, then standard protecting group strategies are contemplated to be applied. For further description of protecting group strategies and procedures, see, for example, Greene, T. W.; Wuts, P. G. M. *Protective Groups in Organic Synthesis*, $2^{nd}$ ed.; Wiley, New York, 1991.

SCHEME 1

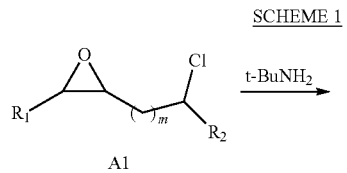

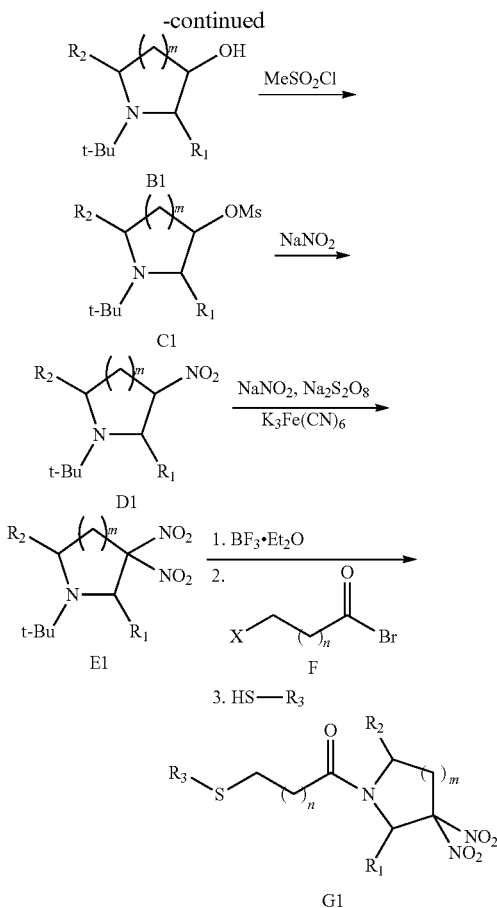

$R_1$ and $R_2$ are, for example, independentyl H, alkyl, or arylalkyl;
X is, for example, halogen, —OCOCF$_3$, or —OSO$_2$R$_4$ wherein R$_4$ is alkyl, aryl, or arylalkyl;
$R_3$ is, for example, a disubstituted alkyl, wherein on substituent is an amino group and the other substituent is a carbonyl-containing group;
n is, for example, 0, 1, or 2; and
m is, for example, 0, 1, or 2.

Scheme 2 illustrates a more specific embodiment of the synthetic route shown in Scheme 1 when m is 0. In the first step, epoxide A2 is reacted with t-butylamine to provide hydroxyl azetidine B2. Mesylation of the hydroxyl group of azetidine B2 with methylsulfonyl chloride gives azetidine mesylate C2, which upon reacting with $NaNO_2$ generates mono-nitro azetidine D2. Further nitration of mono-nitro azetidnine D2 with $NaNO_2$ in the presence of $Na_2S_2O_8$ and K₃Fe(CN)₆ furnishes the geminal di-nitro azetidine E2. A three-step procedure provides di-nitro azetidine G2, which involves reaction of compound E2 with boron trifluoride etherate, acylation with acetyl bromide F, and thiolation to provide di-nitro azetidine G2. This synthetic procedure is contemplated to be applicable to preparing compounds having various substituents at the $R_1$, $R_2$, $R_3$ and $R_4$ positions. If a particular epoxide compound embraced by A2 should contain a functional group sensitive to one or more of the synthetic transformations in Scheme 2, then standard protecting group strategies are contemplated to be applied. For further description of protecting group strategies and procedures, see, for example, Greene, T. W.; Wuts, P. G. M. *Protective Groups in Organic Synthesis*, $2^{nd}$ ed.; Wiley, New York, 1991. Furthermore, mono-nitro compounds can be prepared by treating mono-nitro compound D2 with a Lewis Acid (e.g., boron trifluoride etherate) and acetyl bromide compound F (e.g., from Scheme 2) to provide the desired mono-nitro product.

SCHEME 2

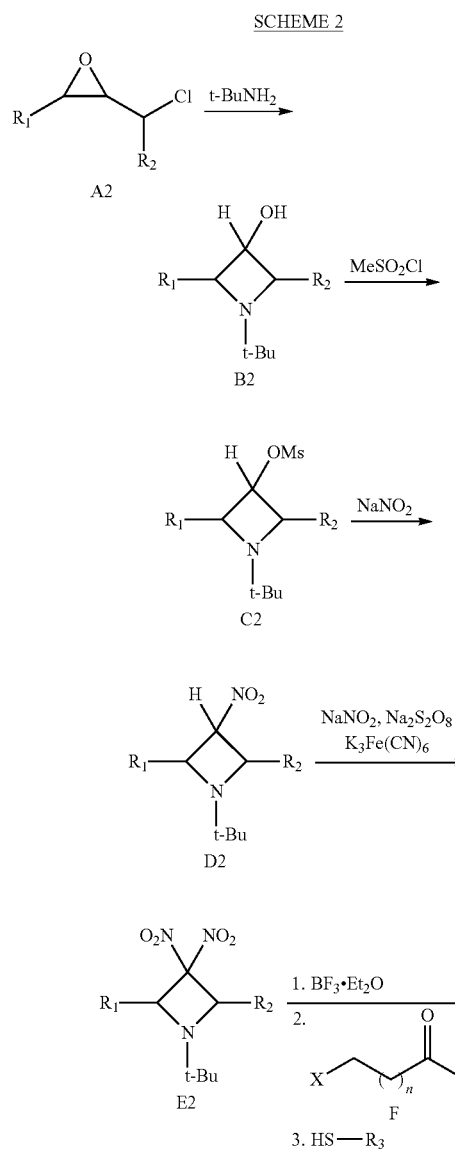

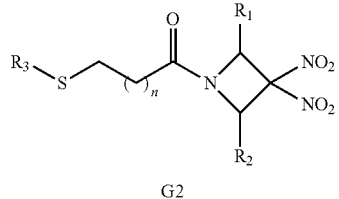

G2

$R_1$ and $R_2$ are, for example, H, alkyl, or arylalkyl;
X is, for example, halogen, —OCOCF₃, or —OSO₂R₄ wherein R₄ is alkyl, aryl, or arylalkyl;
$R_3$ is, for example, a disubstituted alkyl, wherein one substituent is an amino group and the other substituent is a carbonyl-containing group; and
n is 0, 1, 2.

Scheme 3 illustrates another more particular embodiment of the synthetic route shown in Scheme 1 when both $R_1$ and $R_2$ are hydrogen and m is 0. In the first step, commercially available epichlorohydrin A3 is reacted with t-butylamine to provide hydroxyl azetidine B3. Mesylation of the hydroxyl group of azetidine B3 with methylsulfonyl chloride gives azetidine mesylate C3, which upon reacting with NaNO₂ generates mono-nitro azetidine D3. Further nitration of mono-nitro azetidine D3 with NaNO₂ in the presence of Na₂S₂O₈ and K₃Fe(CN)₆ furnishes the geminal di-nitro azetidine E3. A three-step procedure provides di-nitro azetidine F3, which involves reaction of compound E3 with boron trifluoride etherate, acylation with acetyl bromide, and thiolation to provide di-nitro azetidine F3. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. Furthermore, mono-nitro compounds can be prepared by treating mono-nitro compound D3 with a Lewis Acid (e.g., boron trifluoride etherate) and acetyl bromide compound F to provide the desired bromo mono-nitro product, which may be subjected to debromination procedures to replace the bromine atom with a hydrogen.

SCHEME 3

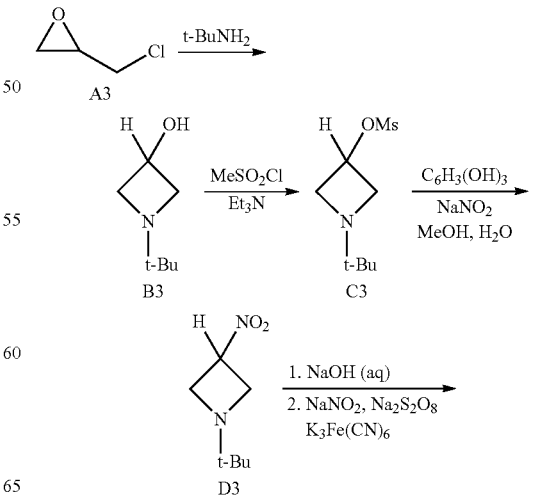

-continued

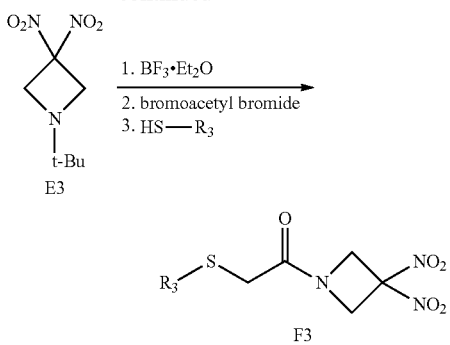

F3

R₃ is, for example, a disubstituted alkyl, wherein one substituent is an amino group and the other substituent is a carbonyl-containing group.

Scheme 4 illustrates an alternative exemplary procedure for preparing cyclic geminal di-nitro compounds. In the first step, heterocyclic compound A4 is reacted with an oxidant, such as pyridinium dichromate (PDC), to provide heterocyclic ketone B4. Reaction of ketone B4 with hydroxylamine gives heterocyclic oxime C4, which upon reaction with N-bromosuccinimide (NBS) produces bromo nitro compound D4. Reaction of compound D4 with NaBH₄ furnishes mono-nitro compound E4. Reaction of mono-nitro compound E4 with NaNO₂ in the presence of Na₂S₂O₈ and K₃Fe(CN)₆ provides geminal di-nitro heterocyclic compound F4. A three-step procedure provides cyclic geminal di-nitro G4, which involves reaction of compound F4 with a deprotecting agent, acylation with acetyl bromide compound F, and thiolation to provide cyclic geminal di-nitro product G4. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. Furthermore, mono-nitro compounds can be prepared by treating mono-nitro compound D4 with a deprotecting agent and acetyl bromide compound F to provide the desired bromo mono-nitro product, which may be subjected to debromination procedures to replace the bromine atom with a hydrogen.

SCHEME 4

P is a protecting group, such as t-butyl or tert-butyl carbamate;
R₁ and R₂ are, for example, independently H, alkyl, or arylalkyl;
X is, for example, halogen, —OCOCF₃, or —OSO₂R₄
wherein R4 is alkyl, aryl, or arylalkyl;
R₃ is, for example, a disubstituted alkyl, wherein one substituent is an amino group and the other substituent is a carbonyl-containing group;
n is, for example, 0, 1 or 2; and
m is, for example, 0, 1, 2, 3, or 4.

Scheme 5 illustrates yet another exemplary procedure for preparing cyclic geminal di-nitro compounds with initial steps different from those shown in Scheme 4. In the first step, heterocyclic compound A4 is reacted with methylsulfonyl chloride to provide heterocyclic mesylate B5. Reaction of mesylate B5 with NaNO₂ gives mono-nitro compound E4. Nitration of compound E4 with NaNO₂ in the presence of Na₂S₂O₈ and K₃Fe(CN)₆ provides geminal di-nitro compound F4. A three-step procedure provides di-nitro compound G4, which involves reaction of compound F4 with a deprotecting agent, acylation with acetyl bromide compound F, and thiolation to provide di-nitro compound G4. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. Furthermore, mono-nitro compounds can be prepared by treating mono-nitro compound E4 with a deprotecting agent and acetyl bromide compound F to provide the desired mono-nitro product.

SCHEME 5

-continued

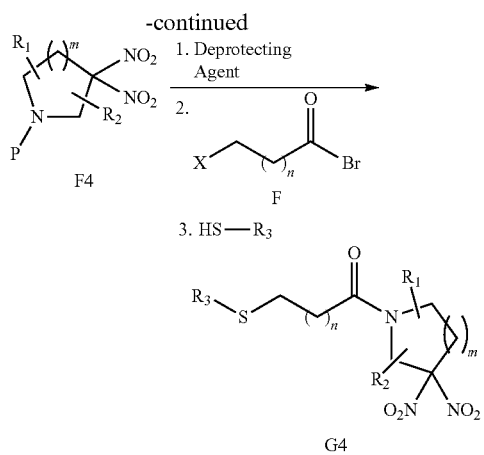

F4

3. HS—R₃

G4

P is a protecting group, such as t-butyl or tert-butyl carbamate;
R₁ and R₂ are, for example, independently H, alkyl, or arylalkyl;
X is, for example, halogen, —OCOCF₃, or —OSO₂R₄
wherein R₄ is alkyl, aryl, or arylalkyl;
R₃ is, for example, a disubstituted alkyl, wherein one substituent is an amino group and the other substituent is a carbonyl-containing group;
n is, for example, 0, 1 or 2; and
m is, for example, 0, 1, 2, 3, or 4.

The synthetic route illustrated in Scheme 6 depicts an exemplary method for preparing cyclic vicinal di-nitro compounds. In the first step, cycloalkene A6 is reacted with N₂O₄ to provide vicinal di-nitro compound B6. A three-step procedure provides vicinal di-nitro product C6, which involves reaction of compound B6 with a deprotecting agent, acylation with acetyl bromide compound F, and thiolation to provide vicinal di-nitro compound C6. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. This synthetic procedure is contemplated to be applicable to preparing compounds having various substituents at the R₁, R₂, R₃ and R₄ positions. If a particular cycloalkene compound embraced by A6 should contain a functional group sensitive to one or more of the synthetic transformations in Scheme 6, then standard protecting group strategies are contemplated to be applied. For further description of protecting group strategies and procedures, see, for example, Greene, T. W.; Wuts, P. G. M. *Protective Groups in Organic Synthesis*, 2$^{nd}$ ed.; Wiley, New York, 1991.

SCHEME 6

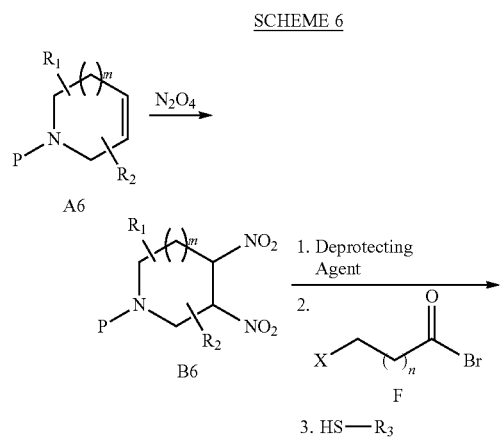

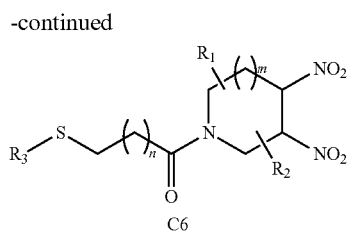

C6

P is a protecting group, such as t-butyl or tert-butyl carbamate;
R₁ and R₂ are, for example, independently H, alkyl, or arylalkyl;
X is, for example, halogen, —OCOCF₃, or —OSO₂R₄
wherein R₄ is alkyl, aryl, or arylalkyl;
R₃ is, for example, a disubstituted alkyl, wherein one substituent is an amino group and the other substituent is a carbonyl-containing group;
n is, for example, 0, 1 or 2; and
m is, for example, 0, 1, 2, 3, or 4.

The synthetic route illustrated in Scheme 7 depicts a general method for preparing cyclic mono-nitro compounds. In the first step, chloro epoxide A7 is reacted with t-butylamine to provide hydroxy heterocyclic compound B7. Mesylation of the hydroxyl group of heterocyclic compound B7 with methylsulfonyl chloride gives mesylate C7 which upon reacting with NaNO₂ generates cyclic mono-nitro compound D7. A three-step procedure provides compound G7, which involves reaction of compound D7 with boron trifluoride etherate, acylation with acetyl bromide compound F, and thiolation to provide compound G7. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. This synthetic procedure illustrated in Scheme 7 is contemplated to be applicable to preparing compounds having various substituents at the R₁, R₂, R₃ and R₄ positions. If a particular epoxide compound embraced by A7 should contain a functional group sensitive to one or more of the synthetic transformations in Scheme 7, then standard protecting group strategies are contemplated to be applied. For further description of protecting group strategies and procedures, see, for example, Greene, T. W.; Wuts, P. G. M. *Protective Groups in Organic Synthesis*, 2$^{nd}$ ed.; Wiley, New York, 1991.

SCHEME 7

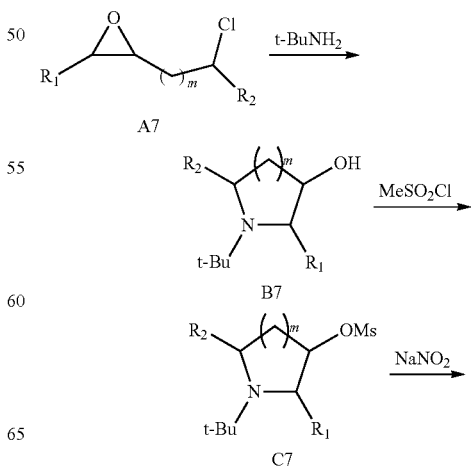

-continued

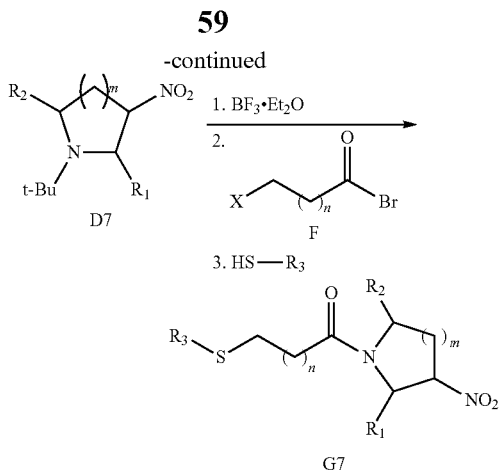

R$_1$ and R$_2$ are, for example, independentyl H, alkyl, or arylalkyl;
X is, for example, halogen, —OCOCF$_3$, or —OSO$_2$R$_4$ wherein R$_4$ is alkyl, aryl, or arylalkyl;
R$_3$ is, for example, a disubstituted alkyl, wherein one substituent is an amino group and the other substituent is a carbonyl-containing group;
n is, for example, 0, 1, or 2; and
m is, for example, 0, 1, or 2.

The synthetic routes described above can be modified to prepare compounds having an alkyl halide attached to the ring nitrogen atom. Exemplary synthetic procedures for preparing such compounds include reducing the amide group of compound G1-G4, G7, and C6 to an amine. Alternatively, compound F used in the procedures above could be replaced with an appropriately protected alkylhalide, such that after the alkylation reaction, the protected alkyl group attached to the ring nitrogen atom is deprotected and converted to an alkyl chloride or bromide.

Scheme 8 depicts another exemplary method for preparing cyclic mono-nitro and di-nitro compounds. Reaction of ketone B8 with hydroxylamine gives heterocyclic hydroxylamine C8, which upon reaction with N-bromosuccinimide (NBS) produces bromo nitro compound D8. Reaction of compound D8 with NaBH$_4$ furnishes mono-nitro compound E8. The hydroxyl protecting group (P, which may be, for example, a tert-butyldimethylsilyl group) and the 1,2-dihydroxyethane protecting group are removed using standard deprotection conditions. Exemplary deprotection conditions for removing a tert-butyldimethyl silyl group include addition of tetra-n-butylammonium fluoride. Exemplary deprotection conditions for removing a 1,2-dihydroxyethane protecting group include addition of hydrochloric acid and water. Hydroxy-ketone F8 can be converted to α-bromo ketone G8 by first reacting compound F8 with methanesulfonyl chloride to form a mesylate and then adding sodium bromide to form α-bromo ketone G8.

Di-nitro compounds can be prepared by reacting mono-nitro compound E8 with NaNO$_2$ in the presence of Na$_2$S$_2$O$_8$ and K$_3$Fe(CN)$_6$ to provide geminal di-nitro heterocyclic compound H8. The hydroxyl protecting group (P, which may be, for example, a tert-butyldimethyl silyl group) and the 1,2-dihydroxyethane protecting group of compound H8 may be removed using standard deprotection conditions. Exemplary deprotection conditions for removing a tert-butyldimethyl silyl group include addition of tetra-n-butylammonium fluoride. Exemplary deprotection conditions for removing a 1,2-dihydroxyethane protecting group include addition of hydrochloric acid and water. Hydroxy-ketone I8 can be converted to α-bromo ketone J8 by first reacting compound I8 with methanesulfonyl chloride to form a mesylate and then adding sodium bromide to form an α-bromo ketone. Thiolation of the α-bromo ketone provides the desired product J8. Further description of related synthetic procedures are described in, for example, Archibald et al. in *J. Org. Chem.* 1990, 55, 2920-2924 and J. P. Agrawal, R. D. Hodgson, *Organic Chemistry of Explosives*, Wiley & Sons, England, 2007 and references cited therein.

SCHEME 8

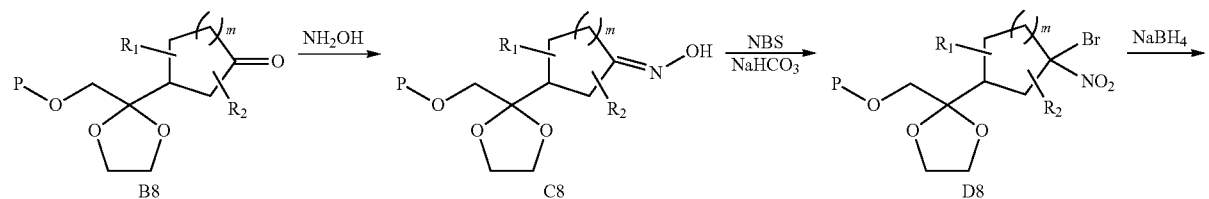

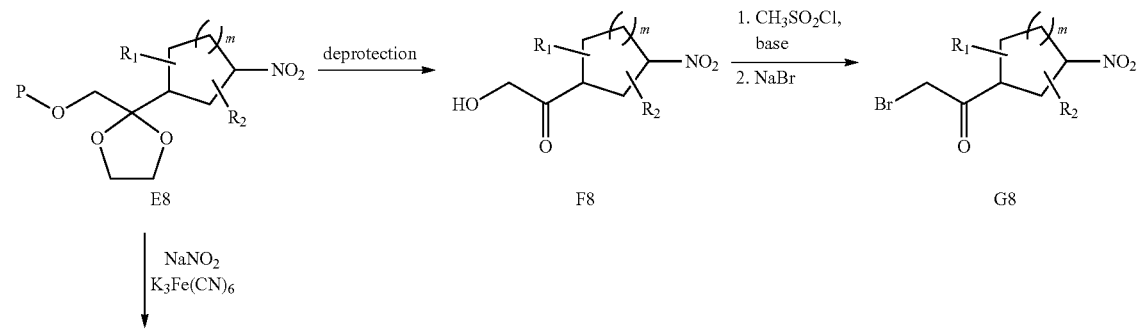

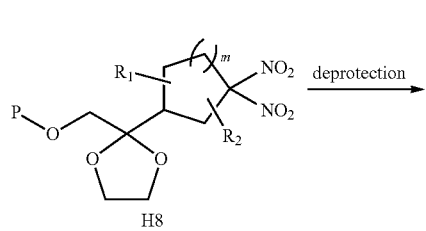 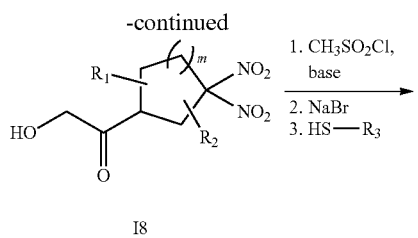 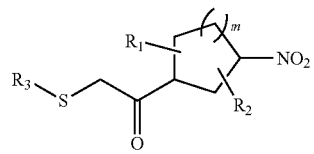

P is a protecting group, such as t-butyl or tert-butyl carbamate;
$R_1$ and $R_2$ are, for example, independently H, alkyl, or arylalkyl;
$R_3$ is, for example, a disubstituted alkyl, wherein one substituent is an amino group and the other substituent is a carbonyl-containing group;
n is, for example, 0, 1 or 2; and
m is, for example, 0, 1, 2, 3, or 4.

Scheme 9 illustrates an exemplary procedure for preparing acyclic geminal di-nitro compounds. In the first step, protected amino alcohol A9 is reacted with methylsulfonyl chloride to provide mesylate B9. Reaction of mesylate B9 with $NaNO_2$ gives mono-nitro compound E9. Nitration of compound E9 with $NaNO_2$ in the presence of $Na_2S_2O_8$ and $K_3Fe(CN)_6$ provides geminal di-nitro compound F9. A three-step procedure provides the desired di-nitro product G9, which involves reaction of compound F9 with a deprotecting agent, acylation with acetyl bromide compound F, and thiolation to provide di-nitro product G9. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein.

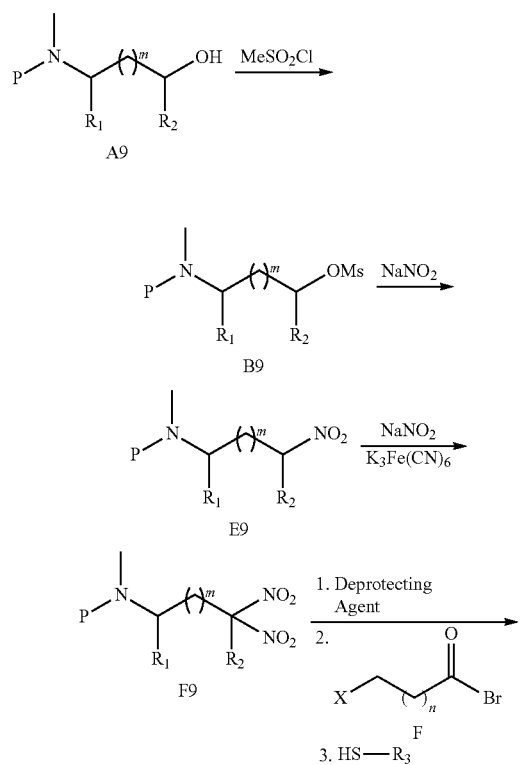

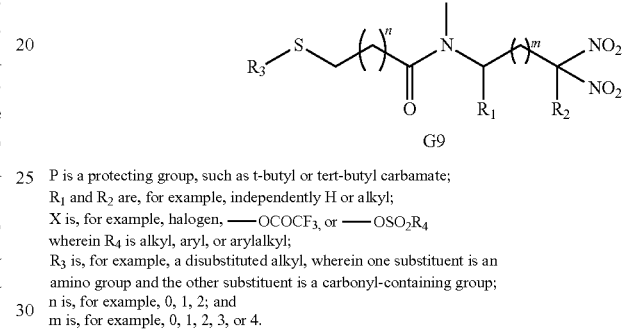

P is a protecting group, such as t-butyl or tert-butyl carbamate;
$R_1$ and $R_2$ are, for example, independently H or alkyl;
X is, for example, halogen, —$OCOCF_3$, or —$OSO_2R_4$ wherein $R_4$ is alkyl, aryl, or arylalkyl;
$R_3$ is, for example, a disubstituted alkyl, wherein one substituent is an amino group and the other substituent is a carbonyl-containing group;
n is, for example, 0, 1, 2; and
m is, for example, 0, 1, 2, 3, or 4.

Scheme 10 illustrates an alternative procedure for preparing mono-nitro compounds. Reaction of dinitro compound A10 with thiol compound B10 provides mono-nitro compound C10. The reaction can be performed at room temperature, or the reaction mixture can be heated to achieve a temperature higher than room temperature. One or more equivalents of thiol B10 may be used, relative to the amount of dinitro compound A10. One exemplary thiol B10 that can be used in the procedure is cysteine. A more specific illustration of this synthetic procedure is the reaction of dinitro compound A10' with cysteine (B10') to provide mono-nitro compound C10'.

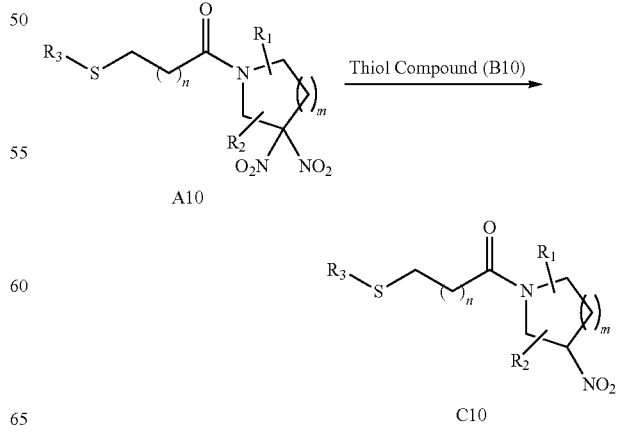

-continued

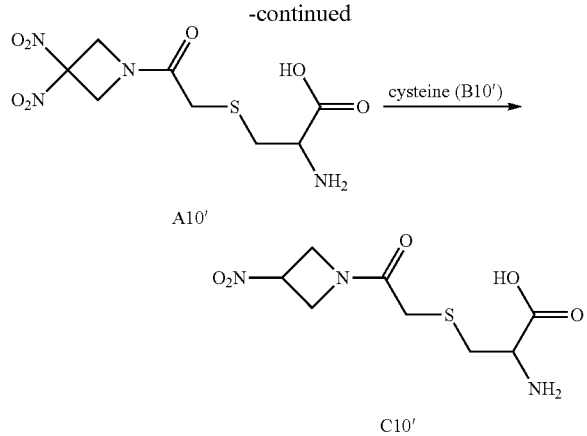

A10'

C10'

R₁ and R₂ are, for example, independently H, alkyl or arylalkyl;
R₃ is, for example, a disubstituted alkyl, wherein one substituent is an amino group and the other substituent is a carbonyl-containing group;
n is, for example, 0, 1 or 2; and
m is, for example, 0, 1, 2, 3, or 4.

III. Therapeutic Applications

The invention provides methods of treating various medical disorders, such as cancer, using the organonitro thioether compounds and pharmaceutical compositions described herein. Treatment methods include the use of organonitro thioether compounds described herein as stand-alone chemotherapeutic agents, as radiation sensitizers, and/or as part of a combination therapy with another therapeutic agent. Although not wishing to be bound by a particular theory, it is understood that organonitro thioether compounds described herein can release reactive free radicals that are cytotoxic to cancer cells.

Methods of Treating Medical Disorders

One aspect of the invention provides a method of treating cancer in a patient. The method comprises administering to a patient in need thereof a therapeutically effective amount of an organonitro thioether compound described herein, such as a compound of Formula I or II, which as described above, Formula I is represented by:

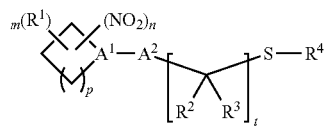
(I)

or a pharmaceutically acceptable salt or solvate thereof, wherein:

$A^1$ is N or —$C(R^5)$—;
$A^2$ is —C(O)— or —$(C(R^6)_2)_x C(O)(C(R^6)_2)_x$—;
$R^1$ is $C_1$-$C_5$alkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —$N(R^7)(R^8)$, —$N(R^7)C(O)$—$C_1$-$C_5$alkyl, —$N(R^7)C(O)$—$C_3$-$C_7$cycloalkyl, —$N(R^7)C(O)$-aryl, —$N(R^7)C(O)$-aralkyl, or —$N(R^7)C(O)$—$(C_1$-$C_5$alkylene)-C(H)[$N(R^7)(R^8)$]—$CO_2R^9$; and $X^2$ is —$CO_2R^{10}$ or —$C(O)N(R^7)$—$(C_1$-$C_5$alkylene)-$CO_2R^{10}$;

$R^5$ is hydrogen or $C_1$-$C_5$alkyl;
$R^6$ represents independently for each occurrence $C_1$-$C_6$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
n, p, and t are independently 1, 2, or 3; and
m and x each represent independently for each occurrence 0, 1, 2, or 3; and Formula II is represented by:

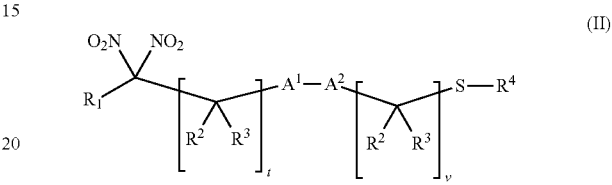
(II)

or a pharmaceutically acceptable salt or solvate thereof:
wherein:
$A^1$ is —$N(R^5)$— or —$C(R^2)(R^3)$—;
$A^2$ is —C(O)— or —$(C(R^6)_2)_x C(O)(C(R^6)_2)_x$—;
$R^1$ is $C_1$-$C_5$alkyl or $C_3$-$C_7$cycloalkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —$N(R^7)(R^8)$, —$N(R^7)C(O)$—$C_1$-$C_5$alkyl, —$N(R^7)C(O)$—$C_3$-$C_7$cycloalkyl, —$N(R^7)C(O)$-aryl, —$N(R^7)C(O)$-aralkyl, or —$N(R^7)C(O)$—$(C_1$-$C_5$alkylene)-C(H)[$N(R^7)(R^8)$]—$CO_2R^9$; and $X^2$ is —$CO_2R^{10}$ or —$C(O)N(R^7)$—$(C_1$-$C_5$alkylene)-$CO_2R^{10}$;
$R^5$ is hydrogen or $C_1$-$C_5$alkyl;
$R^6$ represents independently for each occurrence $C_1$-$C_5$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring; $R^9$ and $R^{10}$ each represent independently hydrogen, $C_1$-$C_5$alkyl, $C_3$-$C_7$cycloalkyl, aryl, or aralkyl;
t and v are independently 1, 2, or 3; and
x represents independently for each occurrence 0, 1, 2, or 3.

In certain embodiments, the cancer is a solid tumor. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The therapeutic methods may optionally comprise exposing the patient to radiation. One exemplary form of radiation is gamma rays, such as those produced from a $^{137}$Cs source. The amount of radiation can be optimized for particular conditions. In certain embodiments, the quantity of radiation applied to the patient is at least about 2 Gy, about 5 Gy, about 10 Gy, or about 15 Gy.

In addition, the therapeutic methods may optionally comprise administering a chemotherapeutic agent to the patient. Exemplary chemotherapeutic agents include azacitidine, azathioprine, bleomycin, carboplatin, capecitabine, carmustine, cisplatin, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, temozolomide, thiotepa, tioguanine, tamoxifen, toremifene, valrubicin, vinblastine, vincristine, vindesine, vinorelbine, and pharmaceutically acceptable salts thereof.

In certain embodiments, the patient is a human.

In certain embodiments, the compound is one of the generic or specific compounds described in Section II, such as a compound of Formula I, a compound embraced by one of the further embodiments describing definitions for certain variables of Formula I, a compound of Formula II, a compound embraced by one of the further embodiments describing definitions for certain variables of Formula II, a compound of Formula IA, or a compound embraced by one of the further embodiments describing definitions for certain variables of Formula IA.

The description above describes multiple embodiments relating to methods of treating various disorders using certain organonitro thioether compounds. The patent application specifically contemplates all combinations of the embodiments. For example, the invention contemplates methods for treating cancer (such as breast cancer, leukemia, or prostate cancer) by administering a therapeutically effective amount of a compound of Formula IA wherein $A^1$ is N, $R^1$ is hydrogen, $R^4$ is —CH$_2$C(H)(X$^1$)X$^2$, and p is 1.

In certain embodiments, the compound is

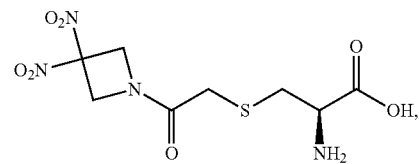

or a pharmaceutically acceptable salt thereof. In certain other embodiments, the compound is

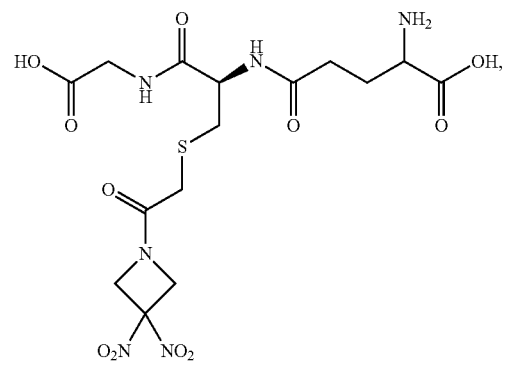 [SMILES: NC(CCC(=O)N[C@@H](CSCC(=O)N1CC([N+](=O)[O-])([N+](=O)[O-])C1)C(=O)NCC(=O)O)C(=O)O]

or a pharmaceutically acceptable salt thereof. In another embodiment, the compound is

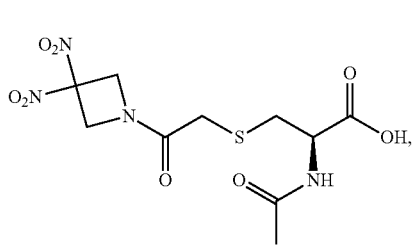 [SMILES: CC(=O)N[C@@H](CSCC(=O)N1CC([N+](=O)[O-])([N+](=O)[O-])C1)C(=O)O]

or a pharmaceutically acceptable salt thereof. In one embodiment, the compound is

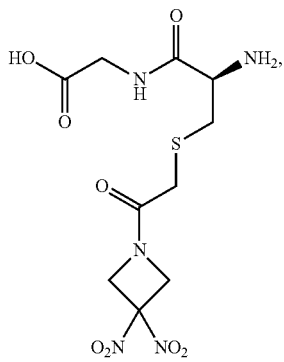

or a pharmaceutically acceptable salt thereof. In certain other embodiments, the compound is

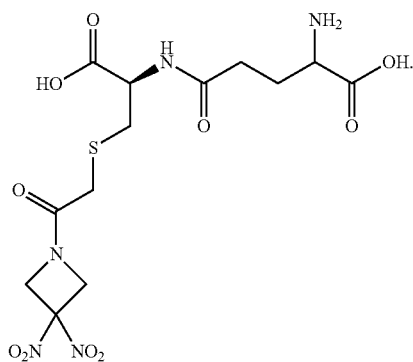 [SMILES: NC(CCC(=O)N[C@@H](CSCC(=O)N1CC([N+](=O)[O-])([N+](=O)[O-])C1)C(=O)O)C(=O)O]

or a pharmaceutically acceptable salt thereof. In certain other embodiments, the compound is

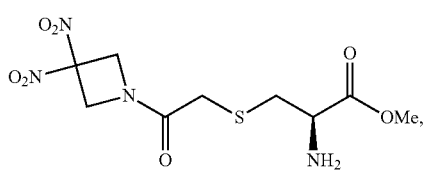 [SMILES: COC(=O)[C@@H](N)CSCC(=O)N1CC([N+](=O)[O-])([N+](=O)[O-])C1]

or a pharmaceutically acceptable salt thereof.

In certain embodiments, the compound is

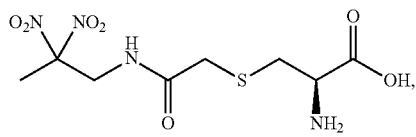 [SMILES: CC(CNC(=O)CSC[C@H](N)C(=O)O)([N+](=O)[O-])[N+](=O)[O-]]

or a pharmaceutically acceptable salt thereof. In certain other embodiments, the compound is

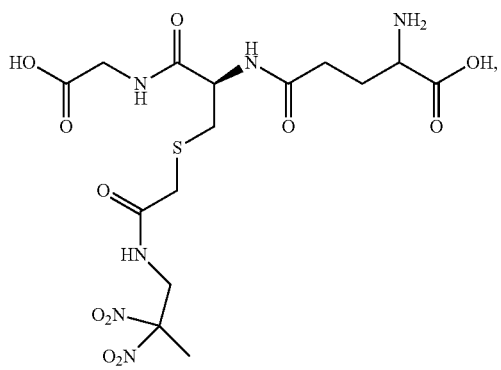

or a pharmaceutically acceptable salt thereof.

Combination Therapy

As indicated above, invention embraces combination therapy, which includes the administration of an organonitro thioether compound described herein (such as compound of Formula I, II or IA) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents. Administration of these therapeutic agents in combination typically is carried out over a defined time period (e.g., hours or days depending upon the combination selected). The combination therapy may involve administration of two or more of these therapeutic agents as part of separate monotherapy regimens that result in the combinations of the present invention. Combination therapy also includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

It is understood that the therapeutic agents can be administered by the same route or by different routes. For example, a first therapeutic agent of the combination selected may be administered by pulmonary administration while the other therapeutic agent(s) of the combination may be administered orally. Alternatively, for example, all therapeutic agents may be administered orally or all therapeutic agents may be administered by pulmonary administration.

Accordingly, in certain embodiments, one or more of the methods described herein above further comprise administering to the patient a therapeutically effective amount of a second therapeutic agent. In certain embodiments, the second therapeutic agent is, for example, adenosine, an antimicrobial compound, an aldosterone antagonist, an alpha-adrenergic receptor antagonist, a β-adrenergic agonist, an anti-allergic compound, an anti-diabetic compound, an anti-hyperlipidemic drug, an anti-tussive compound, an angiotensin II antagonist, an angiotensin-converting enzyme (ACE) inhibitor, an antioxidant, an antithrombotic, a vasodilator drug, a β-adrenergic antagonist, a bronchodilator, a calcium channel blocker, a diuretic, an endothelin antagonist, an expectorant, a hydralazine compound, a H2-receptor antagonist, a neutral endopeptidase inhibitor, a nonsteroidal antiinflammatory compound (NSAID), a phosphodiesterase inhibitor, a potassium channel blocker, a platelet reducing agent, a proton pump inhibitor, a renin inhibitor, a selective cyclooxygenase-2 (COX-2) inhibitor, or a steroid. In certain other embodiments, the second therapeutic agent is selected from the group consisting of an antimicrobial compound, a β-adrenergic agonist, an anti-allergic compound, an anti-tussive compound, an antioxidant, a bronchodilator, an expectorant, a nonsteroidal antiinflammatory compound (NSAID), a phosphodiesterase inhibitor, a selective cyclooxygenase-2 (COX-2) inhibitor, or a steroid.

IV. Pharmaceutical Compositions

The invention provides pharmaceutical compositions comprising a pharmaceutical carrier and an organonitro thioether compound described herein, such as a compound of Formula I or II, which as described above, Formula I is represented by:

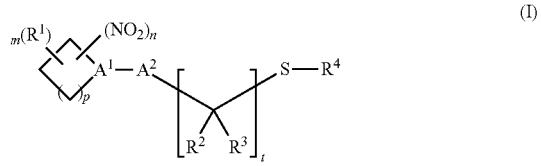

or a pharmaceutically acceptable salt or solvate thereof, wherein:
$A^1$ is N or —C($R^5$)—;
$A^2$ is —C(O)— or —(C($R^6$)$_2$)$_x$C(O)(C($R^6$)$_2$)$_x$—;
$R^1$ is $C_1$-$C_5$alkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —N($R^7$)($R^8$), —N($R^7$)C(O)—$C_1$-$C_5$alkyl, —N($R^7$)C(O)—$C_3$-$C_7$cycloalkyl, —N($R^7$)C(O)-aryl, —N($R^7$)C(O)-aralkyl, or —N($R^7$)C(O)—($C_1$-$C_5$alkylene)-C(H)[N($R^7$)($R^8$)]—$CO_2R^9$; and $X^2$ is —$CO_2R^{10}$ or —C(O)N($R^7$)—($C_1$-$C_5$alkylene)-$CO_2R^{10}$;
$R^5$ is hydrogen or $C_1$-$C_5$alkyl;
$R^6$ represents independently for each occurrence $C_1$-$C_6$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;

n, p, and t are independently 1, 2, or 3; and
m and x each represent independently for each occurrence 0, 1, 2, or 3; and
Formula II is represented by:

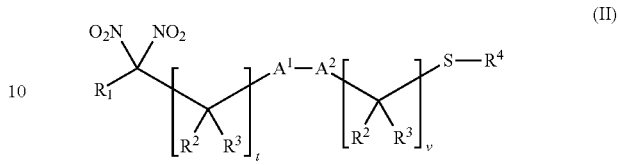

or a pharmaceutically acceptable salt or solvate thereof: wherein:
$A^1$ is —N($R^5$)— or —C($R^2$)($R^3$)—;
$A^2$ is —C(O)— or —(C($R^6$)$_2$)$_x$C(O)(C($R^6$)$_2$)$_x$—;
$R^1$ is $C_1$-$C_5$alkyl or $C_3$-$C_7$cycloalkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —N($R^7$)($R^8$), —N($R^7$)C(O)—$C_1$-$C_5$alkyl, —N($R^7$)C(O)—$C_3$-$C_7$cycloalkyl, —N($R^7$)C(O)-aryl, —N($R^7$)C(O)-aralkyl, or —N($R^7$)C(O)—($C_1$-$C_5$alkylene)-C(H)[N($R^7$)($R^8$)]—$CO_2R^9$; and $X^2$ is —$CO_2R^{10}$ or —C(O)N($R^7$)—($C_1$-$C_5$alkylene)-$CO_2R^{10}$;
$R^5$ is hydrogen or $C_1$-$C_5$alkyl;
$R^6$ represents independently for each occurrence $C_1$-$C_5$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
t and v are independently 1, 2, or 3; and
x represents independently for each occurrence 0, 1, 2, or 3.

In certain embodiments, the organonitro thioether compound is defined by one or more of the particular embodiments described above in Section II, such as where the organonitro thioether compound is a compound Formula I, $A^1$ is N, $R^2$ and $R^3$ are hydrogen, m is 0, and n is 2.

In certain embodiments, the pharmaceutical compositions preferably comprise a therapeutically-effective amount of one or more of the organonitro thioether compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders a compound of the present invention orally bioavailable.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug administered by subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Organonitro thioether compounds and/or pharmaceutical compositions thereof may also be administered directly to the lung by inhalation. For administration by inhalation, organonitro thioether compounds and/or pharmaceutical compositions thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver organonitro thioether compounds and/or pharmaceutical compositions thereof directly to the lung.

Alternatively, a Dry Powder Inhaler ("DPI") device may be used to administer an organonitro thioether compound and/or pharmaceutical composition thereof to the lung. DPI devices typically use a mechanism such as a burst of gas to create a cloud of dry powder inside a container, which may then be inhaled by the patient, and are well known in the art. A popular variation is the multiple dose DPI ("MDDPI") system, which allows for the delivery of more than one therapeutic dose. MDDPI devices are commercially available from a number of pharmaceutical companies (e.g., Schering Plough, Madison, N.J.). For example, capsules and cartridges of gelatin for use in an inhaler or insufflator may be formulated containing a powder mix of an organonitro thioether compound and/or pharmaceutical composition thereof and a suitable powder base such as lactose or starch for these systems.

Another type of device that may be used to deliver a compound and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver an organonitro thioether compound and/or pharmaceutical composition thereof to the lung. Nebulizers create aerosols from liquid drug formulations by using, for example, ultrasonic energy to form fine particles that may be readily inhaled (see e.g., Verschoyle et al., *British J. Cancer,* 1999, 80, Suppl. 2, 96). Examples of nebulizers include devices supplied by Sheffield Pharmaceuticals, St. Louis, Mo. (see, e.g., Armer et al., U.S. Pat. No. 5,954,047; van der Linden et al., U.S. Pat. No. 5,950,619; van der Linden et al., U.S. Pat. No. 5,970,974) and Batelle Pulmonary Therapeutics, Columbus, Ohio.

In other embodiments, an electrohydrodynamic ("EHD") aerosol device is used to deliver an organonitro thioether compound and/or pharmaceutical composition thereof to the lung of a patient. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering an organonitro thioether compound and/or pharmaceutical composition thereof to the lung with an EHD aerosol device and such optimization is routinely performed by one of skill in the art. EHD aerosol devices may more efficiently deliver drugs to the lung than existing pulmonary delivery technologies.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrase "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Kits for Use in Medical Applications

Another aspect of the invention provides a kit for treating a disorder. The kit comprises: i) instructions for treating cancer, such as a cancer selected from the group consisting of brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, and uterine cancer; and ii) an organonitro thioether compound described herein, such as a compound of Formula I or II. The kit may comprise one or more unit dosage forms containing an amount of an organonitro thioether compound described herein, such as a compound of Formula I or II, that is effective for treating said cancer.

The description above describes multiple aspects and embodiments of the invention, including organonitro thioether compounds, compositions comprising organonitro thioether compounds, methods of using the organonitro thioether compound, and kits. The patent application specifically contemplates all combinations and permutations of the aspects and embodiments. For example, the invention contemplates treating cancer in a human patient by administering a therapeutically effective amount of a compound of Formula IA. Further, for example, the invention contemplates a kit for treating cancer, the kit comprising instructions for treating cancer (such as breast cancer, leukemia, or prostate cancer) and ii) an organonitro thioether compound described herein, such as a compound of Formula IA.

EXAMPLES

The invention now being generally described, will be more readily understood by reference to the following examples, which are included merely for purposes of illustration of certain aspects and embodiments of the present invention, and are not intended to limit the invention.

Example 1

Preparation of ABDNAZ-Cysteine (ABDNAZ-Cys)

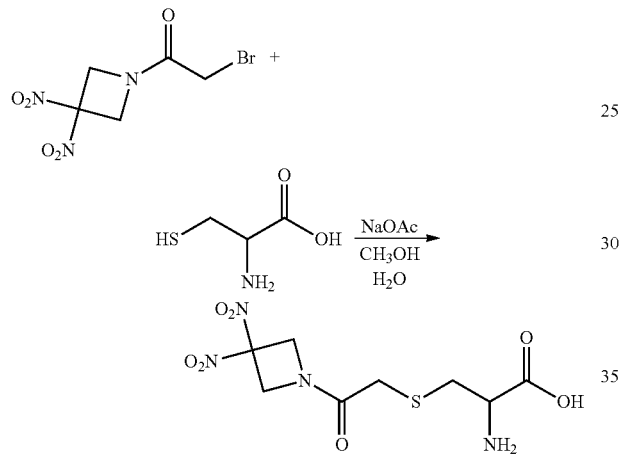

A solution of 2-bromo-1-(3,3-dinitroazetidin-1-yl)ethanone (ABDNAZ, 1340 mg, 5.00 mmol) in cold methanol (30 mL) was added dropwise to a stirred solution of cysteine (610 mg, 5.03 mmol) and sodium acetate (420 mg, 5.12 mmol) in reverse osmosis water (10 mL) and methanol (10 mL) over 30 minutes and maintained at 0-5° C. in a reaction flask. When the addition was complete, a substantial amount of white solid had separated and the reaction flask was closed and maintained at −10° C. for 2 hours. The white solid was separated by filtration, washed with cooled methanol (−10° C.) and then dried at 60° C. to give 910 mg of the title compound as a white solid having a melting point of 150-152° C.

The filtrate and wash was then evaporated to dryness under reduced pressure and the white residue treated with ethanol (10 mL), the flask sealed and allowed to stand for 36 hours. The resultant white solid was removed by filtration, washed with ethanol and dried at 60° C. to give 400 mg of the title compound as a white solid having a melting point of 151-153° C. The infrared spectra of the two products were identical and the combined yield of 1310 mg represented an 85% yield of product. The combined products were recrystallized from water/ethanol (1 to 4) with 88% recovery to give product with an infrared spectrum identical to the product before recrystallization, a single spot on TLC and mp 151-153° C. FTIR (KBr press): 3438.3, 3015.9, 2076.0, 1670.1, 1634.9, 1582.1, 1446.5, 1388.0, 1337.6, and 1304.8 cm$^{-1}$.

ABDNAZ can be prepared as described in U.S. Pat. No. 7,507,842, which is hereby incorporated by reference.

Example 2

Preparation of ABDNAZ-Glutathione

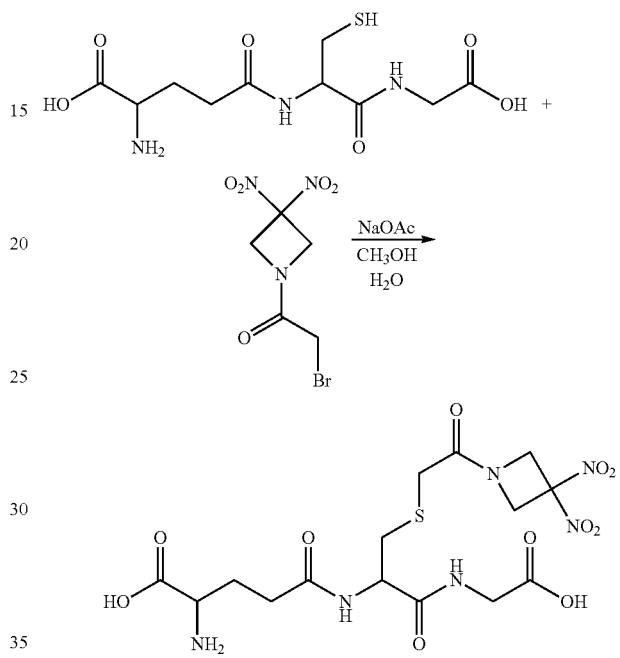

A 40 mL vial equipped with a magnetic stirrer was charged with methanol (20 mL) and deionized water (5 mL). L-Glutathione (0.50 g, 1.63 mmole) was added followed by sodium acetate (0.17 g, 2.07 mmole). The mixture was stirred until the solids dissolved. 2-Bromo-1-(3,3-dinitroazetidin-1-yl) ethanone (ABDNAZ, 0.43 g, 1.60 mmole) was then added to the solution and the reaction was stirred at room temperature for 18 hours. The reaction mixture was then filtered and the solids were washed with methanol (10 mL). The solids were then dried in a vacuum oven at 50° C. for 20 hours to provide the title compound.

Example 3

Preparation of (R)-2-Amino-3-[2-(3,3-Dinitro-Azetidin-1-Yl)-2-Oxoethylsulfanyl]-Propionic Acid Methyl Ester Hydrochloride

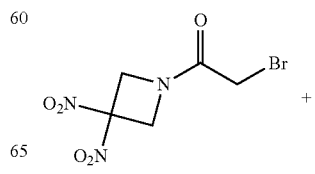

-continued

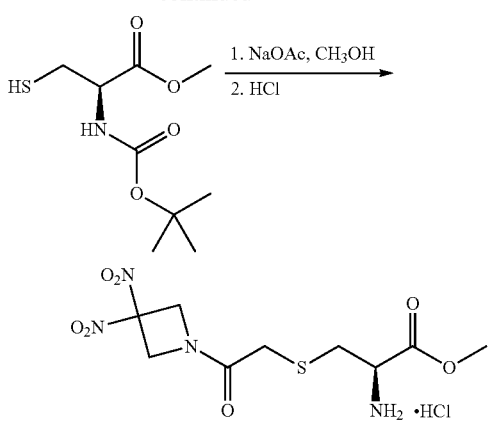

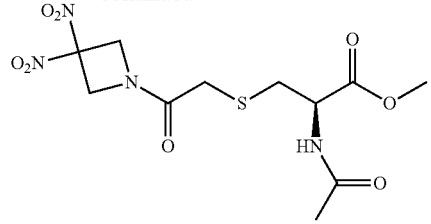

A solution of ABDNAZ (850, 3.17 mmol) in cold (0° C.) methanol (35 mL) was added dropwise to a cold (0° C.) stirred solution of N-Boc-cysteine methyl ester (785 mg, 3.23 mmol) and sodium acetate (265 mg, 3.23 mmol) in methanol (15 mL) and HPLC grade water (15 mL) over 30 mins. After 2 hours, thin-layer chromatography (TLC) showed complete conversion. The mixture was concentrated to dryness under reduced pressure and ethyl acetate was added to the residue and the mixture filtered through celite and the filtrate concentrated under reduced pressure. The crude product was treated with 4 N HCl in dioxane (35 mL) and the resulting mixture was stirred overnight at room temperature. Then, the mixture was concentrated under reduced pressure. Ethyl acetate was added and the solid was filtered and further dried under vacuum to yield 660 mg (65% for two steps) of the title compound as a white solid. $^1$H NMR (200 MHz, $D_2O$) δ 3.09 (dd, 1H, J=8.0, 15.4 Hz), 3.26 (dd, 1H, J=4.8, 15.4 Hz), 3.36 (s, 3H), 3.75 (s, 3H), 4.32 (dd, 1H, J=4.8, 8.0 Hz), 4.89 (bs, 2H), 5.09 (s, 2H), 5.17 (bs, 2H). LC/MS (M+H=323). The purity was checked using LC/MS using Phenomenex Luna 3μ C8 (2) 100 A column using water with 0.1% TFA and acetonitrile with 0.1% as mobile phase (30-90% acetonitrile @ 1.0 mL/min). Retention time=0.45 mins; Area %=97.9%.

Example 4

Preparation of (R)-Methyl 2-Acetamido-3-(2-(3,3-Dinitroazetidin-1-Yl)-2-Oxoethylthio)Propanoate

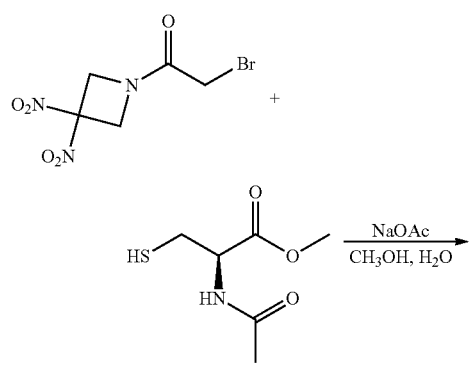

A solution of ABDNAZ (474 mg, 1.77 mmol) in cold (0° C.) methanol (20 mL) was added dropwise to a cold (0° C.) stirred solution of N-acetylcysteine methyl ester (320 mg, 1.80 mmol) and sodium acetate (148 mg, 1.80 mmol) in methanol (5 mL) and HPLC grade water (5 mL) over 30 mins. After 2 hours, TLC showed complete conversion. The mixture was concentrated to dryness under reduced pressure and ethyl acetate was added to the residue and the mixture filtered through celite. The filtrate was concentrated under reduced pressure and the residue purified by column chromatography on silica gel (using 50% ethyl acetate in hexanes to pure ethyl acetate as eluent) to yield 515 mg (80%) of the title compound as a white foam. $^1$H NMR (200 MHz, $CDCl_3$) δ 2.04 (s, 3H), 2.97 (dd, 1H, J=7.4, 14.8 Hz), 3.19 (dd, 1H, J=4.8, 14.8 Hz), 3.24 (s, 2H), 3.78 (s, 3H), 5.13-4.83 (m, 5H), 6.48 (d, 1H, J=7.4 Hz). LC/MS (M+H=365 and M+Na=387). The purity was checked using LC/MS using Phenomenex Luna 3μ C8 (2) 100 A column using water with 0.1% TFA and acetonitrile with 0.1% as mobile phase (30-90% acetonitrile @ 1.0 mL/min). Retention time=0.87 mins; Area %=100%.

Example 5

Preparation of (R)-2-Acetamido-3-(2-(3,3-Dinitroazetidin-1-Yl)-2-Oxoethylthio)Propanoic Acid

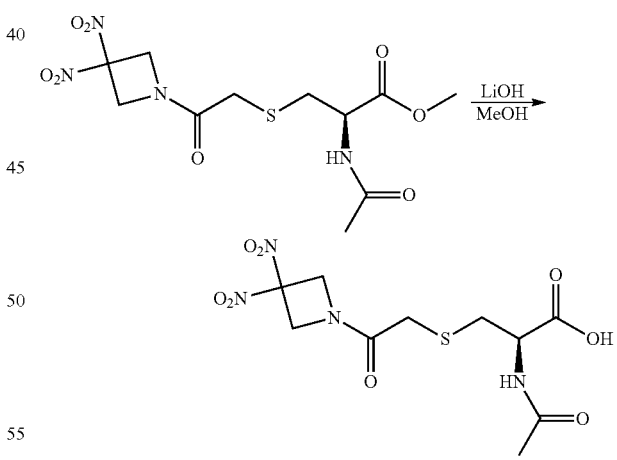

(R)-Methyl 2-acetamido-3-(2-(3,3-dinitroazetidin-1-yl)-2-oxoethylthio)propanoate (1.02 g, 2.80 mmol) was dissolved in methanol (50 mL) with stirring and the mixture cooled to 0° C. Then, LiOH (0.5 M, 8.40 mL) was added dropwise to the reaction mixture via a syringe and the resulting yellow mixture stirred until TLC showed complete conversion (2.5 hours). Next, the reaction mixture was diluted with water, cooled to 0° C. and acidified to pH=2 with a 50% HCl solution. Then, the reaction mixture was extracted with ethyl acetate (×2) and the extracts were dried over $Na_2SO_4$, filtered and concentrated under reduced pressure to provide a residue that was purified by column chromatography using silica gel and 30% MeOH in EtOAc as eluent to provide the title compound 625 mg (64%) as a white solid. $^1$H NMR (200 MHz, DMSO-d$^6$) δ 1.85 (s, 3H), 2.81 (dd, 1H, J=8.4, 13.6 Hz), 3.04 (dd, 1H, J=4.8, 13.6 Hz), 3.33 (s, 2H), 4.41-4.35 (m, 1H), 4.80 (s, 2H), 5.13 (s, 2H), 8.20 (d, 1H, J=8.0 Hz). LC/MS (M+H=351). The purity was checked using LC/MS using Phenomenex Luna 3μ C8 (2) 100 A column using water with 0.1% TFA and acetonitrile with 0.1% as mobile phase (30-90% acetonitrile @ 1.0 mL/min). Retention time=0.60 mins; Area %=97.6%.

Example 6

Anti-Cancer Assay

Mice with SCC VII tumors were treated with Compound 1, which has the following chemical structure.

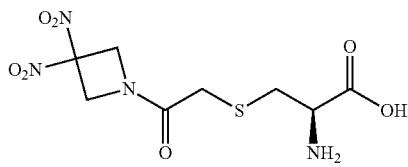

(1)

Experimental procedures and results are provided below.
Part I: Experimental Procedure
Treatment Composition:

The Treatment Composition was Compound 1 in a water/DMSO carrier. The Treatment Composition was prepared by dissolving 2.3 mg of Compound 1 in 0.1 mL of DMSO and mixing the resultant solution with 1.9 mL of water to provide a solution containing 1.15 mg/mL of Compound 1. The concentration of dimethylsulfoxide (DMSO) in the Treatment Composition was 5%.
Study Procedures:

Male C3H mice were obtained from Charles River Laboratories and maintained under specific pathogen-free conditions. Mice were housed five animals per cage and autoclaved food and water was provided ad libitum. Cages were located in rooms having a temperature of 65±2 degrees Fahrenheit, a humidity of 50%±5%, and a 12-hour day-and-night light cycle. Mice were 7-8 weeks old, with a body weight in the range of 22-25 grams, at the time inoculated with tumor cells.

Mice were inoculated subcutaneously with 5×10$^5$ SCCVII tumor cells in 0.05 mL Hank's solution on the back. Ten days after tumor implantation, treatment was initiated (Day 0) by administering the Treatment Composition by intraperitoneal injection every other day (i.e., q.o.d on Days 0, 2, and 4) for 3 doses total. The length and width of the tumors were measured with calipers immediately before treatment and three times a week thereafter until the tumor volume reached at least four times (4×) the original pre-treatment volume. Tumor volume (mm$^3$) was calculated according to the formula:

Tumor Volume=π/6×length×width$^2$

Part II: Results

Tumors in mice that received the Treatment Composition were smaller than tumors in mice that did not receive the Treatment Composition (i.e., the control). Experimental data showing tumor volume in treated and untreated (control) mice are provided in FIG. 1.

Example 7

Toxicity Evaluation Healthy Rats

Compound 1 was administered to healthy rats and the rats were evaluated for evidence of toxic side effects due to Compound 1. Experimental procedures and results are described below. The results indicate that no significant toxicity was observed in rats receiving Compound 1.

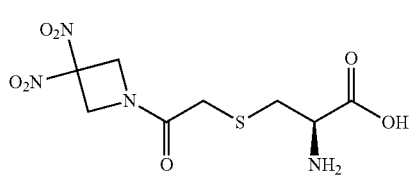

(1)

Part I: Experimental Procedure

Two groups of 3 male rats each were given a 100 or 300 mg/kg dose of Compound 1 prepared in 0.9% saline solution. A third group of 3 rats were given saline alone. Doses were delivered via a femoral vein. The 100 mg/kg dose was delivered using a 10 mg/mL solution at a dose volume of 10 mL/kg and an infusion rate of 15 mL/hr. The 300 mg/kg dose was delivered using a 20 mg/mL solution at a dose volume of 15 mL/kg and an infusion rate of 15 mL/hr. Animals were observed for 24 hours, necropsied (and the pleural and abdominal cavities were observed grossly), and the lungs collected for possible microscopic evaluation.
Part II: Results No notable clinical observations were found in rats that received the 100 mg/kg dose of Compound 1. Rats that received the 300 mg/kg dose of Compound 1 were observed to be pale during the first 3 hours post dose. There were no gross changes in the lungs of rats that received Compound 1. Mottled kidneys were observed in most rats that received Compound 1, but further evaluation would be required to determine if this observation has significance for measuring the toxicity of Compound 1.

Incorporation By Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition comprising a pharmaceutically acceptable carrier and an organonitro compound of Formula I or II, wherein Formula I is represented by:

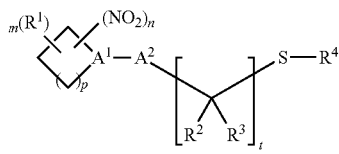

or a pharmaceutically acceptable salt or solvate thereof, wherein:

$A^1$ is N or —$C(R^5)$—;
$A^2$ is —$C(O)$— or —$(C(R^6)_2)_xC(O)(C(R^6)_2)_x$—;
$R^1$ is $C_1$-$C_5$alkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —$N(R^7)(R^8)$, —$N(R^7)C(O)$—$C_1$-$C_5$alkyl, —$N(R^7)C(O)$—$C_3$-$C_7$cycloalkyl, —$N(R^7)C(O)$-aryl, —$N(R^7)C(O)$—aralkyl, or —$N(R^7)C(O)$—($C_1$-$C_5$alkylene)-$C(H)[N(R^7)(R^8)]$—$CO_2R^9$; and $X^2$ is —$CO_2R^{10}$ or —$C(O)N(R^7)$—($C_1$-$C_5$alkylene)-$CO_2R^{10}$;
$R^5$ is hydrogen or $C_1$-$C_5$alkyl;
$R^6$ represents independently for each occurrence $C_1$-$C_6$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
n, p, and t are independently 1, 2, or 3; and
m and x each represent independently for each occurrence 0, 1, 2, or 3;
Formula II is represented by:

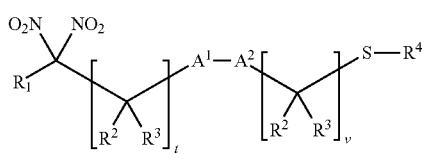

or a pharmaceutically acceptable salt or solvate thereof:
wherein:
$A^1$ is —$N(R^5)$— or —$C(R^2)(R^3)$—;
$A^2$ is —$C(O)$— or —$(C(R^6)_2)_xC(O)(C(R^6)_2)_x$—;
$R^1$ is $C_1$-$C_5$alkyl or $C_3$-$C_7$cycloalkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —$N(R^7)(R^8)$, —$N(R^7)C(O)$—$C_1$-$C_5$alkyl, —$N(R^7)C(O)$—$C_3$-$C_7$cycloalkyl, —$N(R^7)C$(O)-aryl, —$N(R^7)C(O)$—aralkyl, or —$N(R^7)C(O)$—($C_1$-$C_5$alkylene)-$C(H)[N(R^7)(R^8)]$—$CO_2R^9$; and $X^2$ is —$CO_2R^{10}$ or —$C(O)N(R^7)$—($C_1$-$C_5$alkylene)-$CO_2R^{10}$;
$R^5$ is hydrogen or $C_1$-$C_5$alkyl;
$R^6$ represents independently for each occurrence $C_1$-$C_5$alkyl, $C_1$-$C_5$haloalkyl, aryl, or aralkyl;

$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
t and v are independently 1, 2, or 3; and
x represents independently for each occurrence 0, 1, 2, or 3.

2. The pharmaceutical composition of claim 1, wherein the organonitro compound is a compound of Formula I.

3. The pharmaceutical composition of claim 2, wherein $A^1$ is N.

4. The pharmaceutical composition of claim 3, wherein $A^2$ is —$C(O)$—.

5. The pharmaceutical composition of claim 4, wherein $R^2$ and $R^3$ are hydrogen.

6. The pharmaceutical composition of claim 5, wherein m is 0.

7. The pharmaceutical composition of claim 4, wherein n is 2.

8. The pharmaceutical composition of claim 7, wherein t is 1.

9. The pharmaceutical composition of claim 7, wherein $R^4$ is —$CH_2C(H)(X^1)X^2$.

10. The pharmaceutical composition of claim 9, wherein $X^1$ is —$N(R^7)(R^8)$, —$N(R^7)C(O)$—$C_1$-$C_5$alkyl, or —$N(R^7)C(O)$—($C_1$-$C_5$alkylene)-$C(H)[N(R^7)(R^8)]CO_2R^9$.

11. The pharmaceutical composition of claim 9, wherein $X^1$ is —$NH_2$, —$N(H)C(O)CH_3$, or —$N(H)C(O)CH_2CH_2C(H)(NH_2)$—$CO_2H$; and $X^2$ is —$CO_2H$, —$CO_2Me$, or —$C(O)N(H)CH_2CO_2H$.

12. The pharmaceutical composition of claim 9, wherein $X^1$ is —$NH_2$ or —$N(H)C(O)CH_2CH_2C(H)(NH_2)$—$CO_2H$; and $X^2$ is —$CO_2H$ or —$C(O)N(H)CH_2CO_2H$.

13. The pharmaceutical composition of claim 7, wherein $R^4$ is

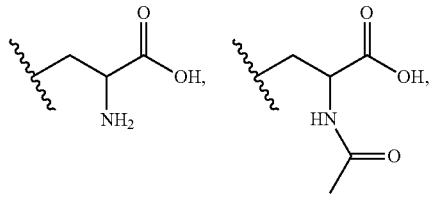

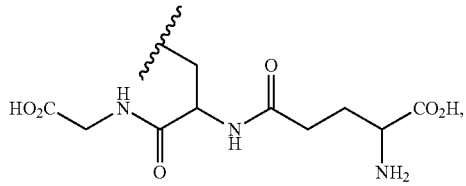

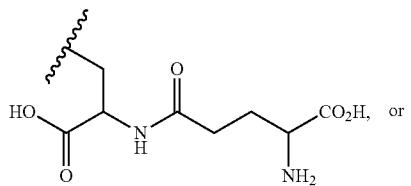

or

-continued

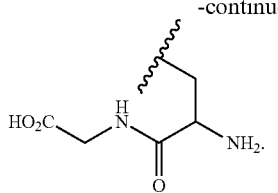

14. The pharmaceutical composition of claim 1, wherein the organonitro compound is a compound of Formula I-A:

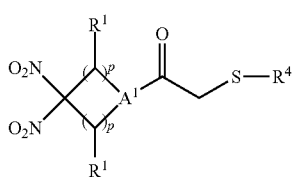

(I-A)

or a pharmaceutically acceptable salt or solvate thereof, wherein:
$A^1$ is N or C(H);
$R^1$ represents independently for each occurrence hydrogen or methyl;
$R^4$ is $C_1$-$C_5$alkyl substituted with one $X^1$ group and one $X^2$ group; wherein $X^1$ is —$NH_2$, —N(H)C(O)—$C_1$-$C_5$alkyl, or —N(H)C(O)—($C_1$-$C_5$alkylene)-C(H)($NH_2$)—$CO_2H$; and $X^2$ is —$CO_2H$, —$CO_2$—$C_1$-$C_5$alkyl, or —C(O)N(H)$CH_2CO_2H$; and
p represents independently for each occurrence 1 or 2.

15. The pharmaceutical composition of claim 14, wherein $R^4$ is

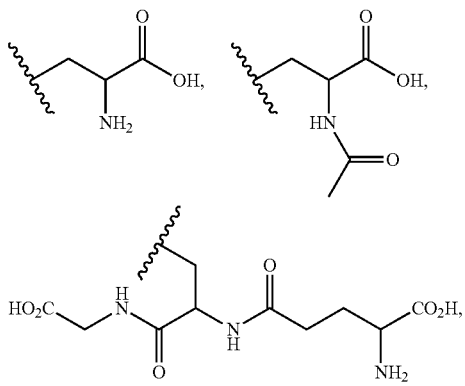

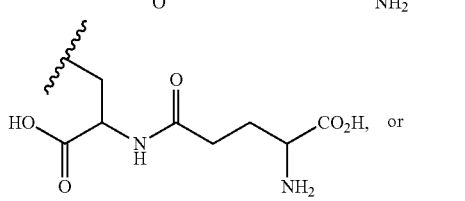

or

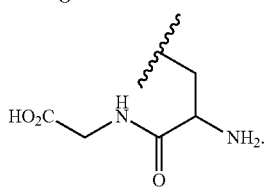

16. The pharmaceutical composition of claim 1, wherein the organonitro compound is one of the following:

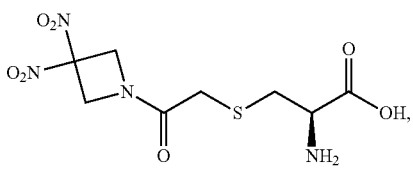

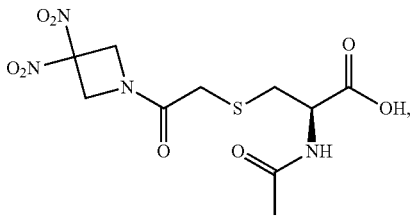

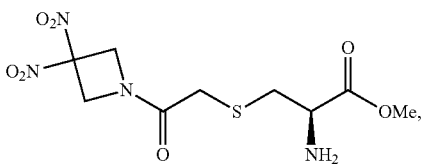

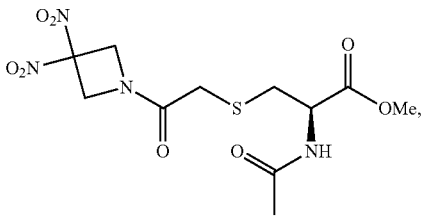

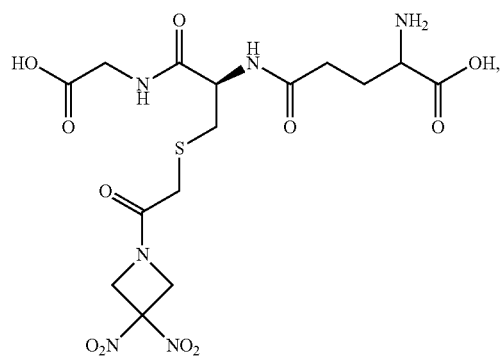

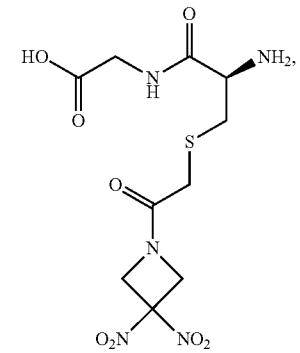

-continued

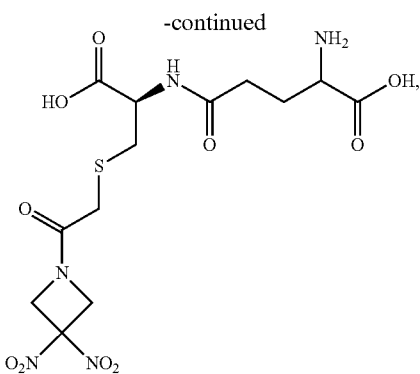

or a pharmaceutically acceptable salt thereof.

17. An isolated compound of Formula I, wherein Formula 1 is represented by:

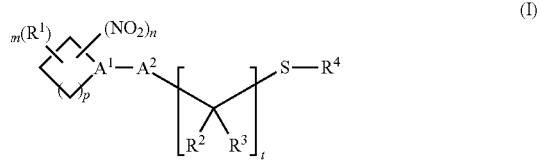

(I)

or a pharmaceutically acceptable salt or solvate thereof, wherein:

$A^1$ is N or —C($R^5$)—;
$A^2$ is —C(O)— or —(C($R^6$)$_2$)$_x$C(O)(C($R^6$)$_2$)$_x$—;
$R^1$ is $C_1$-$C_5$alkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —N($R^7$)($R^8$), —N($R^7$)C(O)—$C_1$-$C_5$alkyl, —N($R^7$)C(O)—$C_3$-$C_7$cycloalkyl, —N($R^7$)C(O)-aryl, —N($R^7$)C(O)-aralkyl, or —N($R^7$)C(O)—($C_1$-$C_5$alkylene)-C(H)[N($R^7$)($R^8$)]—$CO_2R^9$; and $X^2$ is —$CO_2R^{10}$ or —C(O)N($R^7$)—($C_1$-$C_5$alkylene)-$CO_2R^{10}$;
$R^5$ is hydrogen or $C_1$-$C_5$alkyl;
$R^6$ represents independently for each occurrence $C_1$-$C_6$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
n, p, and t are independently 1, 2, or 3; and
m and x each represent independently for each occurrence 0, 1, 2, or 3.

18. A compound of Formula II, wherein Formula II is represented by:

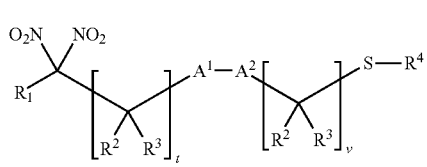

(II)

or a pharmaceutically acceptable salt or solvate thereof: wherein:

$A^1$ is —N($R^5$)— or —C($R^2$)($R^3$)—;
$A^2$ is —C(O)— or —(C($R^6$)$_2$)$_x$C(O)(C($R^6$)$_2$)$_x$—;
$R^1$ is $C_1$-$C_5$alkyl or $C_3$-$C_7$cycloalkyl;
$R^2$ and $R^3$ each represent independently for each occurrence hydrogen or $C_1$-$C_5$alkyl; or $R^2$ and $R^3$ are taken together with the carbon atom to which they are attached to form a carbocyclic ring;
$R^4$ is $C_1$-$C_5$alkyl substituted with one $X^1$ group and one $X^2$ group; wherein $X^1$ is —N($R^7$)($R^8$), —N($R^7$)C(O)—$C_1$-$C_5$alkyl, —N($R^7$)C(O)—$C_3$-$C_7$cycloalkyl, —N($R^7$)C(O)-aryl, —N($R^7$)C(O)-aralkyl, or —N($R^7$)C(O)—($C_1$-$C_5$alkylene)-C(H)[N($R^7$)($R^8$)]$CO_2R^9$; and $X^2$ is —$CO_2R^{10}$ or —C(O)N($R^7$)—($C_1$-$C_5$alkylene)-$CO_2R^{10}$;
$R^5$ is hydrogen or $C_1$-$C_5$alkyl;
$R^6$ represents independently for each occurrence $C_1$-$C_5$alkyl, $C_1$-$C_5$haloalkyl, aryl, or aralkyl;
$R^7$ and $R^8$ each represent independently for each occurrence hydrogen or $C_1$-$C_5$alkyl; or $R^7$ and $R^8$ are taken together with the nitrogen atom to which they are attached to form a 3-7 membered heterocyclic ring;
$R^9$ and $R^{10}$ each represent independently hydrogen, $C_1$-$C_5$alkyl, $C_3$-$C_7$cycloalkyl, aryl, or aralkyl;
t and v are independently 1, 2 or 3; and
x represents independently for each occurrence 0, 1, 2 or 3.

19. A method of treating cancer in a patient, comprising administering to a patient in need thereof a therapeutically effective amount of a pharmaceutical composition of claim 1.

20. The method of claim 19, wherein the cancer is a solid tumor.

21. The method of claim 19, wherein the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer.

22. The method of claim 19, further comprising exposing the cancer to radiation.

23. The method of claim 19, further comprising administering a chemotherapeutic agent to the patient.

24. The method of claim 19, wherein the patient is a human.

* * * * *